(12) United States Patent
Cook

(10) Patent No.: US 11,806,075 B2
(45) Date of Patent: Nov. 7, 2023

(54) ACTIVE ALIGNMENT SYSTEM AND METHOD FOR LASER OPTICAL COUPLING

(71) Applicant: BOLT MEDICAL, INC., Carlsbad, CA (US)

(72) Inventor: Christopher A. Cook, Laguna Niguel, CA (US)

(73) Assignee: Bolt Medical, Inc., Carlsbad, CA (US)

( * ) Notice: Subject to any disclaimer, the term of this patent is extended or adjusted under 35 U.S.C. 154(b) by 0 days.

(21) Appl. No.: 17/831,056

(22) Filed: Jun. 2, 2022

(65) Prior Publication Data
US 2022/0387106 A1  Dec. 8, 2022

Related U.S. Application Data

(60) Provisional application No. 63/197,959, filed on Jun. 7, 2021.

(51) Int. Cl.
*A61B 18/22* (2006.01)
*A61M 25/01* (2006.01)
(Continued)

(52) U.S. Cl.
CPC ......... *A61B 18/22* (2013.01); *A61M 25/0105* (2013.01); *A61B 2018/00107* (2013.01);
(Continued)

(58) Field of Classification Search
CPC ........ A61B 18/22; A61B 2018/205547; A61B 2018/00107; A61B 2018/2261; A61M 25/0105; A61M 2025/0166
See application file for complete search history.

(56) References Cited

U.S. PATENT DOCUMENTS

| 4,649,924 A | 3/1987 | Taccardi |
| 4,699,147 A | 10/1987 | Chilson et al. |

(Continued)

FOREIGN PATENT DOCUMENTS

| AU | 2017205323 | 1/2022 |
| AU | 2019452180 | 1/2022 |

(Continued)

OTHER PUBLICATIONS

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

(Continued)

*Primary Examiner* — Carl H Layno
*Assistant Examiner* — Aya Ziad Bakkar
(74) *Attorney, Agent, or Firm* — ROEDER & BRODER LLP; James P. Broder

(57) ABSTRACT

A catheter system for treating site within or adjacent to a vessel wall or a heart valve includes a light source, a first and second light guide, and an optical alignment system. The light source generates light energy. The first and second light guides receive the light energy from the light source and have respective guide proximal ends. A multiplexer directs the light energy toward the guide proximal ends of the first and second light guides. The optical alignment system determines an alignment of the light energy relative to at least one of the guide proximal ends and adjusts the positioning of the light energy relative to the at least one of the guide proximal ends based at least partially on the alignment of the light energy relative to the at least one of the guide proximal ends.

20 Claims, 6 Drawing Sheets

(51) Int. Cl.
  *A61B 18/00* (2006.01)
  *A61B 18/20* (2006.01)
(52) U.S. Cl.
  CPC ............ *A61B 2018/205547* (2017.05); *A61B 2018/2261* (2013.01); *A61M 2025/0166* (2013.01)

(56) References Cited

U.S. PATENT DOCUMENTS

| | | | |
|---|---|---|---|
| 4,799,479 A | 1/1989 | Spears | |
| 4,913,142 A | 4/1990 | Kittrell et al. | |
| 4,932,954 A | 6/1990 | Wondrazek et al. | |
| 4,955,895 A | 9/1990 | Sugiyama | |
| 4,960,108 A | 10/1990 | Reichel et al. | |
| 4,994,059 A | 2/1991 | Kosa et al. | |
| 5,034,010 A * | 7/1991 | Kittrell ............ A61B 1/00096 600/478 |
| 5,041,121 A | 8/1991 | Wondrazek et al. | |
| 5,104,391 A | 4/1992 | Ingle | |
| 5,104,392 A | 4/1992 | Kittrell et al. | |
| 5,116,227 A | 5/1992 | Levy | |
| 5,152,768 A | 10/1992 | Bhatta | |
| 5,173,049 A | 12/1992 | Levy | |
| 5,181,921 A | 1/1993 | Makita et al. | |
| 5,200,838 A | 4/1993 | Nudelman | |
| 5,290,277 A | 3/1994 | Vercimak et al. | |
| 5,324,282 A | 6/1994 | Dodick | |
| 5,372,138 A | 12/1994 | Crowley | |
| 5,387,225 A | 2/1995 | Euteneur | |
| 5,400,428 A | 3/1995 | Grace | |
| 5,422,926 A | 6/1995 | Smith | |
| 5,454,809 A | 10/1995 | Janssen | |
| 5,509,917 A | 4/1996 | Cecchetti | |
| 5,540,679 A | 7/1996 | Fram | |
| 5,562,657 A | 10/1996 | Griffin | |
| 5,598,494 A | 1/1997 | Behrmann et al. | |
| 5,609,606 A | 3/1997 | O'Boyle | |
| 5,611,807 A | 3/1997 | O'Boyle | |
| 5,697,377 A | 12/1997 | Wittkamph | |
| 5,718,241 A | 2/1998 | Ben-Haim et al. | |
| 5,729,583 A | 3/1998 | Tang | |
| 5,772,609 A | 6/1998 | Nguyen et al. | |
| 5,860,974 A | 1/1999 | Abele | |
| 5,891,135 A | 4/1999 | Jackson et al. | |
| 5,906,611 A | 5/1999 | Dodick et al. | |
| 5,944,697 A | 8/1999 | Benett et al. | |
| 6,015,404 A | 1/2000 | Altshuler | |
| 6,080,119 A | 6/2000 | Schwarze et al. | |
| 6,123,923 A | 9/2000 | Unger | |
| 6,139,510 A | 10/2000 | Palermo | |
| 6,186,963 B1 | 2/2001 | Schwarze et al. | |
| 6,203,537 B1 | 3/2001 | Adrian | |
| 6,210,404 B1 | 4/2001 | Shadduck | |
| 6,339,470 B1 | 1/2002 | Papademetriou et al. | |
| 6,368,318 B1 | 4/2002 | Visuri et al. | |
| 6,500,174 B1 | 12/2002 | Maguire et al. | |
| 6,514,203 B2 | 2/2003 | Bukshpan | |
| 6,514,249 B1 | 2/2003 | Maguire | |
| 6,524,251 B2 | 3/2003 | Rabiner et al. | |
| 6,538,739 B1 | 3/2003 | Visuri et al. | |
| 6,607,502 B1 | 8/2003 | Maguire et al. | |
| 6,652,547 B2 | 11/2003 | Rabiner et al. | |
| 6,666,834 B2 | 12/2003 | Restle et al. | |
| 6,773,447 B2 | 8/2004 | Laguna | |
| 6,849,994 B1 | 2/2005 | White et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,309,324 B2 | 12/2007 | Hayes et al. | |
| 7,470,240 B2 | 12/2008 | Schultheiss et al. | |
| 7,569,032 B2 | 8/2009 | Naimark et al. | |
| 7,599,588 B2 | 10/2009 | Eberle et al. | |
| 7,713,260 B2 | 5/2010 | Lessard | |
| 7,758,572 B2 | 7/2010 | Weber et al. | |
| 7,810,395 B2 | 10/2010 | Zhou | |
| 7,850,685 B2 | 12/2010 | Kunis et al. | |
| 7,867,178 B2 | 1/2011 | Simnacher | |
| 7,972,299 B2 | 7/2011 | Carter | |
| 7,985,189 B1 | 7/2011 | Ogden et al. | |
| 8,162,859 B2 | 4/2012 | Schultheiss et al. | |
| 8,166,825 B2 | 5/2012 | Zhou | |
| 8,192,368 B2 | 6/2012 | Woodruff | |
| 8,292,913 B2 | 10/2012 | Warnack | |
| 8,328,820 B2 | 12/2012 | Diamant | |
| 8,364,235 B2 | 1/2013 | Kordis et al. | |
| 8,419,613 B2 | 4/2013 | Saadat | |
| 8,439,890 B2 | 5/2013 | Beyar | |
| 8,556,813 B2 | 10/2013 | Cashman et al. | |
| 8,574,247 B2 | 11/2013 | Adams et al. | |
| 8,657,814 B2 | 2/2014 | Werneth | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Tawkins et al. | |
| 8,986,339 B2 | 3/2015 | Warnack | |
| 8,992,817 B2 | 3/2015 | Stamberg | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Adams et al. | |
| 9,131,949 B2 | 9/2015 | Coleman et al. | |
| 9,138,249 B2 | 9/2015 | Adams et al. | |
| 9,138,260 B2 | 9/2015 | Miller et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,289,132 B2 | 3/2016 | Ghaffari et al. | |
| 9,289,224 B2 | 3/2016 | Adams et al. | |
| 9,320,530 B2 | 4/2016 | Grace | |
| 9,333,000 B2 | 5/2016 | Hakala et al. | |
| 9,375,223 B2 | 6/2016 | Wallace | |
| 9,421,025 B2 | 8/2016 | Hawkins et al. | |
| 9,433,428 B2 | 9/2016 | Hakala et al. | |
| 9,504,809 B2 | 11/2016 | Bo | |
| 9,510,887 B2 | 12/2016 | Burnett | |
| 9,522,012 B2 | 12/2016 | Adams | |
| 9,554,815 B2 | 1/2017 | Adams et al. | |
| 9,555,267 B2 | 1/2017 | Ein-gal | |
| 9,566,209 B2 | 2/2017 | Katragadda et al. | |
| 9,579,114 B2 | 2/2017 | Mantell et al. | |
| 9,629,567 B2 | 4/2017 | Porath et al. | |
| 9,642,673 B2 | 5/2017 | Adams | |
| 9,662,069 B2 | 5/2017 | De Graff et al. | |
| 9,687,166 B2 | 6/2017 | Subramaniam | |
| 9,730,715 B2 | 8/2017 | Adams | |
| 9,764,142 B2 | 9/2017 | Imran | |
| 9,814,476 B2 | 11/2017 | Adams et al. | |
| 9,861,377 B2 | 1/2018 | Mantell et al. | |
| 9,867,629 B2 | 1/2018 | Hawkins et al. | |
| 9,894,756 B2 | 2/2018 | Weinkam et al. | |
| 9,955,946 B2 | 5/2018 | Miller et al. | |
| 9,974,963 B2 | 5/2018 | Imran | |
| 9,974,970 B2 | 5/2018 | Nuta et al. | |
| 9,993,292 B2 | 6/2018 | Adams et al. | |
| 10,039,561 B2 | 8/2018 | Adams et al. | |
| 10,136,829 B2 | 11/2018 | Deno et al. | |
| 10,149,690 B2 | 12/2018 | Hawkins et al. | |
| 10,159,505 B2 | 12/2018 | Hakala et al. | |
| 10,194,994 B2 | 2/2019 | Deno et al. | |
| 10,201,387 B2 | 2/2019 | Grace et al. | |
| 10,206,698 B2 | 2/2019 | Hakala et al. | |
| 10,226,265 B2 | 3/2019 | Ku et al. | |
| 10,357,264 B2 | 7/2019 | Kat-Kuoy | |
| 10,405,923 B2 | 9/2019 | Yu et al. | |
| 10,406,031 B2 | 9/2019 | Thyzel | |
| 10,420,569 B2 | 9/2019 | Adams | |
| 10,441,300 B2 | 10/2019 | Hawkins | |
| 10,478,202 B2 | 11/2019 | Adams et al. | |
| 10,517,620 B2 | 12/2019 | Adams | |
| 10,517,621 B1 | 12/2019 | Hakala et al. | |

(56) References Cited

U.S. PATENT DOCUMENTS

| | | |
|---|---|---|
| 10,537,287 B2 | 1/2020 | Braido et al. |
| 10,555,744 B2 | 2/2020 | Nguyen et al. |
| 10,561,428 B2 | 2/2020 | Eggert et al. |
| 10,646,240 B2 | 5/2020 | Betelia et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,758,255 B2 | 9/2020 | Adams |
| 10,842,567 B2 | 11/2020 | Grace et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 2001/0016761 A1 | 8/2001 | Rudie |
| 2001/0051784 A1 | 12/2001 | Brisken |
| 2002/0045811 A1 | 4/2002 | Kittrell et al. |
| 2002/0065512 A1 | 5/2002 | Fjield et al. |
| 2002/0082553 A1 | 6/2002 | Duchamp |
| 2002/0183729 A1 | 12/2002 | Farr et al. |
| 2002/0188204 A1 | 12/2002 | McNamara et al. |
| 2003/0009157 A1 | 1/2003 | Evine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0176873 A1 | 9/2003 | Chernenko et al. |
| 2004/0002677 A1 | 1/2004 | Gentsler |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142819 A1 | 6/2007 | El-Nounou et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0299392 A1 | 12/2007 | Beyar et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0195088 A1 | 8/2008 | Farr et al. |
| 2008/0214891 A1 | 9/2008 | Slenker et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0192495 A1 | 7/2009 | Ostrovsky et al. |
| 2009/0247945 A1 | 10/2009 | Levit |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160903 A1 | 6/2010 | Krespi |
| 2010/0168572 A1 | 7/2010 | Sliwa |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0095335 A1 | 4/2012 | Sverdlik et al. |
| 2012/0095461 A1 | 4/2012 | Terscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0157892 A1 | 6/2012 | Reitmajer et al. |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0116714 A1 | 5/2013 | Adams et al. |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |

(56) References Cited

U.S. PATENT DOCUMENTS

| | | |
|---|---|---|
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0357997 A1 | 12/2014 | Hartmann |
| 2015/0005576 A1 | 1/2015 | Diodone et al. |
| 2015/0039002 A1 | 2/2015 | Hawkins |
| 2015/0073430 A1 | 3/2015 | Hakala et al. |
| 2015/0080875 A1 | 3/2015 | Kasprzyk et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0141764 A1 | 5/2015 | Harks et al. |
| 2015/0250542 A1 | 9/2015 | Islam |
| 2015/0276689 A1 | 10/2015 | Watanabe et al. |
| 2015/0313732 A1 | 11/2015 | Fulton, III |
| 2015/0359432 A1 | 12/2015 | Ehrenreich |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0143522 A1 | 5/2016 | Ransbury |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184570 A1 | 6/2016 | Grace et al. |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0049877 A1 | 2/2018 | Venkatasubramanian |
| 2018/0092763 A1 | 4/2018 | Dagan et al. |
| 2018/0098779 A1 | 4/2018 | Betelia et al. |
| 2018/0152568 A1 | 6/2018 | Kat-kuoy |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0099588 A1 | 4/2019 | Ramanath et al. |
| 2019/0104933 A1 | 4/2019 | Stern |
| 2019/0117242 A1 | 4/2019 | Lawinger |
| 2019/0150960 A1 | 5/2019 | Nguyen et al. |
| 2019/0175111 A1 | 6/2019 | Genereux et al. |
| 2019/0175300 A1 | 6/2019 | Horn |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0328259 A1 | 10/2019 | Deno et al. |
| 2019/0365400 A1 | 12/2019 | Adams et al. |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046949 A1 | 2/2020 | Chisena et al. |
| 2020/0054352 A1 | 2/2020 | Brouillette et al. |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0107960 A1 | 4/2020 | Bacher |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook |
| 2021/0153939 A1 | 5/2021 | Cook |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0386479 A1 | 12/2021 | Massimini et al. |

(56) References Cited

U.S. PATENT DOCUMENTS

| | | |
|---|---|---|
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Aser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |

FOREIGN PATENT DOCUMENTS

| | | | | |
|---|---|---|---|---|
| CA | 2229806 | 3/1997 | | |
| CA | 2983655 | 10/2016 | | |
| CN | 102057422 | 5/2011 | | |
| CN | 109223100 | 1/2019 | | |
| CN | 110638501 A | 1/2020 | | |
| CN | 106794043 | 3/2020 | | |
| CN | 107411805 | 1/2022 | | |
| CN | 107899126 | 1/2022 | | |
| CN | 109475378 | 1/2022 | | |
| CN | 113876388 | 1/2022 | | |
| CN | 113877044 | 1/2022 | | |
| CN | 113907838 | 1/2022 | | |
| CN | 113951972 A | 1/2022 | | |
| CN | 113951973 A | 1/2022 | | |
| CN | 113974765 | 1/2022 | | |
| CN | 113974826 A | 1/2022 | | |
| CN | 113993463 | 1/2022 | | |
| CN | 215384399 | 1/2022 | | |
| CN | 215386905 | 1/2022 | | |
| CN | 215458400 | 1/2022 | | |
| CN | 215458401 | 1/2022 | | |
| CN | 215505065 | 1/2022 | | |
| CN | 215534803 | 1/2022 | | |
| CN | 215537694 | 1/2022 | | |
| CN | 215584286 | 1/2022 | | |
| CN | 215606068 | 1/2022 | | |
| CN | 215651393 | 1/2022 | | |
| CN | 215651394 | 1/2022 | | |
| CN | 215651484 | 1/2022 | | |
| CN | 215653328 | 1/2022 | | |
| DE | 3038445 A1 | 5/1982 | | |
| DE | 3836337 A1 | 4/1990 | | |
| DE | 3913027 A1 | 10/1990 | | |
| DE | 202008016760 | 3/2009 | | |
| DE | 102007046902 | 4/2009 | | |
| DE | 102008034702 | 1/2010 | | |
| DE | 102009007129 | 8/2010 | | |
| DE | 202010009899 | 11/2010 | | |
| DE | 102013201928 | 8/2014 | | |
| DE | 102020117713 | 1/2022 | | |
| EP | 0119296 | 9/1984 | | |
| EP | 0261831 B1 | 6/1992 | | |
| EP | 558297 A2 | 9/1993 | | |
| EP | 0571306 A1 | 11/1993 | | |
| EP | 1179993 A1 | 2/2002 | | |
| EP | 1946712 | 7/2008 | | |
| EP | 1946712 A1 | 7/2008 | | |
| EP | 2157569 | 2/2010 | | |
| EP | 2879595 | 6/2015 | | |
| EP | 2879595 A1 | 6/2015 | | |
| EP | 2944264 A1 | 6/2015 | | |
| EP | 3226795 A1 | 10/2017 | | |
| EP | 3318204 | 5/2018 | | |
| EP | 3461438 A1 | 4/2019 | | |
| EP | 3473195 A1 | 4/2019 | | |
| EP | 3643260 A1 | 4/2020 | | |
| EP | 3076881 B1 | 1/2022 | | |
| EP | 3932342 | 1/2022 | | |
| EP | 3936140 | 1/2022 | | |
| EP | 4051154 | 9/2022 | | |
| GB | 1082397 | 9/1967 | | |
| JP | S62275446 A | 11/1987 | | |
| KR | 20050098932 | 10/2005 | | |
| KR | 20080040111 | 5/2008 | | |
| KR | 20160090877 A | 8/2016 | | |
| WO | WO9007904 A1 | 7/1990 | | |
| WO | WO9105332 A1 | 4/1991 | | |
| WO | 9203095 A1 | 3/1992 | | |
| WO | WO9208515 | 5/1992 | | |
| WO | 1999002095 A1 | 1/1999 | | |
| WO | 1999020189 A1 | 4/1999 | | |
| WO | WO200067648 | 11/2000 | | |
| WO | WO2000067648 A1 | 11/2000 | | |
| WO | WO0103599 A2 | 1/2001 | | |
| WO | 20060006169 A2 | 1/2006 | | |
| WO | WO2006006169 | 1/2006 | | |
| WO | WO2009121017 | 10/2009 | | |
| WO | WO2009149321 A1 | 12/2009 | | |
| WO | WO2009152352 A2 | 12/2009 | | |
| WO | 2010042653 A1 | 4/2010 | | |
| WO | WO2011094379 | 8/2011 | | |
| WO | 20110126580 A2 | 10/2011 | | |
| WO | WO2012025833 | 3/2012 | | |
| WO | WO20120052924 A1 | 4/2012 | | |
| WO | WO20120120495 A2 | 9/2012 | | |
| WO | WO2013119662 | 8/2013 | | |
| WO | 20130169807 A1 | 11/2013 | | |
| WO | WO2013169807 | 11/2013 | | |
| WO | WO2014025397 A1 | 2/2014 | | |
| WO | WO20140022867 A1 | 2/2014 | | |
| WO | WO2014138582 | 9/2014 | | |
| WO | WO2015056662 | 4/2015 | | |
| WO | WO2015097251 A2 | 7/2015 | | |
| WO | 20150177790 A1 | 11/2015 | | |
| WO | WO2016089683 A1 | 6/2016 | | |
| WO | WO2016090175 | 6/2016 | | |
| WO | WO2016109739 | 7/2016 | | |
| WO | WO2016151595 A1 | 9/2016 | | |
| WO | WO20170192869 A1 | 11/2017 | | |
| WO | 20180022641 A1 | 2/2018 | | |
| WO | WO2018022593 A1 | 2/2018 | | |
| WO | WO2018083666 | 5/2018 | | |
| WO | 20180175322 A1 | 9/2018 | | |
| WO | WO2018175322 | 9/2018 | | |
| WO | WO2018191013 | 10/2018 | | |
| WO | WO2019200201 A1 | 10/2019 | | |
| WO | WO2019222843 | 11/2019 | | |
| WO | WO2020056031 | 3/2020 | | |
| WO | WO20200086361 A1 | 4/2020 | | |
| WO | WO2020089876 A1 | 5/2020 | | |
| WO | WO2020157648 | 8/2020 | | |
| WO | WO2020256898 | 12/2020 | | |
| WO | WO2020256898 A1 | 12/2020 | | |
| WO | WO2020256949 | 12/2020 | | |
| WO | WO2020256949 A1 | 12/2020 | | |
| WO | WO2020263469 A1 | 12/2020 | | |
| WO | WO2020263685 A1 | 12/2020 | | |
| WO | WO2020263687 A1 | 12/2020 | | |
| WO | WO2020263688 A1 | 12/2020 | | |
| WO | WO2020263689 A1 | 12/2020 | | |
| WO | WO2021061451 | 4/2021 | | |
| WO | WO2021067563 | 4/2021 | | |
| WO | WO-2021067563 A1 * | 4/2021 | ............ | A61B 1/043 |
| WO | WO2021086571 A1 | 5/2021 | | |
| WO | WO2021096922 A1 | 5/2021 | | |
| WO | WO2021101766 | 5/2021 | | |
| WO | WO2021101766 A1 | 5/2021 | | |
| WO | WO2021126762 A1 | 6/2021 | | |
| WO | WO2021150502 A1 | 7/2021 | | |

(56) References Cited

FOREIGN PATENT DOCUMENTS

| WO | WO2021162855 A1 | 8/2021 |
|---|---|---|
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022187058 | 9/2022 |
| WO | WO2022216488 | 10/2022 |
| WO | WO2022240674 | 11/2022 |
| WO | WO2022260932 | 12/2022 |

OTHER PUBLICATIONS

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCI excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.

Hardy, L., et al. "Cavitation Bubble Dynamics during Thulium Fiber Laser Lithotripsy", SPIE BIOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, dated Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, dated Jan. 16, 2019.
European Search Report, for European Patent Application No. 18185152.8, dated Dec. 20, 2018.
International Search Report and Written Opinion dated Jul. 29, 2020 in PCT Application Serial No. PCT/US2020/034005.

(56) References Cited

OTHER PUBLICATIONS

International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
International Search Report and Written Opinion dated Nov. 8, 2022 in PCT Application Serial No. PCTUS/2022/039678.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery Of Atrial Endocardial Potential Maps From Non-contact Electrode Data." Auckland Bioengineering Institute. (ID 1421).
Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368).
Sacher et al., "Comparison Of Manual Vs Automatic Annotation To Identify Abnormal Substrate For Scar Related VT Ablation." LIRYC Institute, Bordeaux University Hospital, France (ID 1336).
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion dated Aug. 20, 2021 in PCT Application Serial No. PCT/US2021/031130.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
McAteer, James A., et al. "Ultracal-30 Gypsum Artificial Stones For Research On The Mechinisms Of Stone Breakage In Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 677-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies A Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.

(56) References Cited

OTHER PUBLICATIONS

Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'Nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work On A Sub-Millimeter Spark-Gap For Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 898-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustica Society of America.
Vogel, A., et al. "Shock-Wave Energy and Acoustic Energy Dissipation After Laser-induced Breakdown", SPIE, 1998, pp. 180-189, vol. 3254, SPIE.
International Search Report and Written Opinion, issued by the EP/ISA, in PCT/US2021/048819, dated Jan. 14, 2022.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
Medlight, "Cylindrical light diffuser Model RD-ML", Medlight S.A., Switzerland. 2015.
Medlight, "Cylindircal light diffuser Model RD", Medlight S.A., Switzerland. 2015.
Ohl, Siew-Wan, et al. "Bubbles with shock waves and ultrasound: a review", Interface Focus, pp. 1-15, vol. 5, The Royal Society Publishing. Oct. 2015.
Schafter+Kirchhoff, Laser Beam Couplers series 60SMS for coupling into single-mode and polarization-maintaining fiber cables, Schafter+Kirchhoff, pp. 1-5, Germany. Dec. 2, 2021.
Meng et al., "Accurate Recovery Of Atrial Endocardial Potential Maps From Non-contact Electrode Data." Auckland Bioengineering Institute. (ID 1421). May 2019.
Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019.
Sacher et al., "Comparison Of Manual Vs Automatic Annotation To Identify Abnormal Substrate For Scar Related VT Ablation." LIRYC Institute, Bordeaux University Hospital, France (ID 1336). Poster for conference in San Francisco, May 8-11, 2019.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.

(56) References Cited

OTHER PUBLICATIONS

Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.

Ali, Ziad A., et al. "Intravascular lithotripsy for treatment of stent underexpansion secondary to severe coronary calcification" 2018, European Society of Cardiology.

Ashok, Praveen C., et al. "Raman spectroscopy bio-sensor for tissue discrimination in surgical robotics—full article", Journal of Biophotonics, 2014, pp. 103-109, vol. 7, No. 1-2.

Ashok, Praveen C., et al. "Raman spectroscopy bio-sensor for tissue discrimination in surgical robotics—proof" Journal of Biophotonics 7, 2014, No. 1-2.

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

Bian, D. C., et al. "Study on Breakdown Delay Characteristics Based on High-voltage Pulse Discharge in Water with Hydrostatic Pressure", Journal of Power Technologies 97(2), 2017, pp. 89-102.

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.

Brodmann, Marianne et al. "Safety and Performance of Lithoplasty for Treatment of Calcified Peripheral Artery Lesions", JACC, 2017, vol. 70, No. 7.

Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.

"Bubble Dynamics and Shock Waves", Springer, 2013, Springer-Verlag, Berlin Heildelberg.

Hardy, Luke A., et al. "Cavitation Bubble Dynamics During Thulium Fiber Laser Lithotripsy", SPIE, Feb. 29, 2016, vol. 9689, San Francisco, California, USA.

Claverie, A., et al. "Experimental characterization of plasma formation and shockwave propagation induced by high power pulsed underwater electrical discharge", Review of Scientific Instruments, 2014, American Institute of Physics.

Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and On Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method For Fabricating Artificial Kidney Stones Of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

(56) References Cited

OTHER PUBLICATIONS

Jan Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
International Search Report and Written Opinion dated Aug. 25, 2022 in PCT Application Serial No. PCTUS/2022/028035.
International Search Report and Written Opinion dated Sep. 15, 2022 in PCT Application Serial No. PCTUS/2022/032045.
International Search Report and Written Opinion, PCT Application Serial No. PCT/US2022/047751 dated Feb. 10, 2023, by the European Patent Office. (56PCT).
AccuCoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023. (Re 45PCT).
International Search Report and Written Opinion issued by the European Patent Office, for Serial No. PCT/US2023/011497, dated Apr. 28, 2023. (Re 54PCT).
International Search Report and Written Opinion issued by the European Patent Office, for Serial No. PCT/US2023/012599, dated May 19, 2023. (Re 57PCT).

\* cited by examiner

ACTIVE ALIGNMENT SYSTEM AND METHOD FOR LASER OPTICAL COUPLING

RELATED APPLICATION

This Application is related to and claims priority on U.S. Provisional Patent Application Ser. No. 63/197,959 filed on Jun. 7, 2021, and entitled "ACTIVE ALIGNMENT SYSTEM AND METHOD FOR LASER OPTICAL COUPLING." To the extent permissible, the contents of U.S. Provisional Application Ser. No. 63/197,959 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, and vascular graft bypass, to name a few. Such interventions may not always be ideal or may require subsequent treatment to address the lesion.

SUMMARY

The present invention is directed toward a catheter system for treating a treatment site within or adjacent to a vessel wall or a heart valve. In various embodiments, the catheter system includes a light source, a first light guide, a second light guide, and an optical alignment system. The light source generates light energy. The first light guide receives the light energy from the light source, the first light guide has a guide proximal end. The second light guide receives the light energy from the light source, the second light guide has a guide proximal end. A multiplexer directs the light energy toward the guide proximal end of the first light guide and the guide proximal end of the second light guide. An optical alignment system determines an alignment of the light energy relative to at least one of the guide proximal ends. The optical alignment system adjusts the positioning of the light energy relative to the at least one of the guide proximal ends based at least partially on the alignment of the light energy relative to the at least one of the guide proximal ends.

In some embodiments, the optical alignment system is configured to improve optical coupling between the light energy and at least one of the light guides.

In certain embodiments, the optical alignment system further includes an image sensor that senses the alignment of the light energy relative to at least one of the guide proximal ends, the image sensor being configured to provide a visualization of the alignment.

In various embodiments, the catheter system further includes a system controller that is configured to control the optical alignment system so that the light energy is substantially coupled to the at least one of the guide proximal ends.

In some embodiments, at least one of the light guides is an optical fiber.

In certain embodiments, the light source is a laser.

In various embodiments, the optical alignment system further includes an optical aligner that is configured to align the light energy with the at least one of the guide proximal ends.

In some embodiments, the optical aligner is controlled by the system controller.

In certain embodiments, the optical alignment system further includes an imaging system including an imaging sensor, the imaging system being configured to capture images of a focal point of the light source, and the at least one of the guide proximal ends.

In various embodiments, the imaging system is configured to simultaneously capture images of the focal point of the light source and a scattered energy beam scattered off the at least one of the guide proximal ends.

In some embodiments, the imaging system is configured to utilize an image reference frame that allows direct computation of distance offset from the center of the at least one of the guide proximal ends.

In certain embodiments, the imaging system is configured to determine the offset and compute compensation adjustment of the alignment of the light energy relative to the at least one of the guide proximal ends.

In various embodiments, the optical alignment system further includes an alignment positioner that positions the alignment of the light energy relative to the at least one of the guide proximal ends based on a computed compensation adjustment to substantially couple the light source and the at least one of the guide proximal ends.

In some embodiments, the catheter system further includes a system controller that is configured to control an optics mover that positions the multiplexer and aligns the light energy relative to the at least one of the guide proximal ends.

In certain embodiments, the catheter system further includes a light source mover coupled to the multiplexer, the light source mover being connected to the optics mover so that the optics mover can position the multiplexer along the light source mover.

In various embodiments, the system controller is configured to align the light source into one of (i) a third light guide that receives the light energy from the light source, the third light guide having a guide proximal end, and (ii) a third light guide that receives the light energy from the light source, the third light guide having a guide proximal end.

In some embodiments, the light source is a pulsed IR laser.

In certain embodiments, the multiplexer further includes optical elements including a dichroic beamsplitter that splits the light source into at least two light beams.

In various embodiments, the dichroic beamsplitter is configured to reflect a reflected light energy with a shorter wavelength than the light energy emitted by the light source.

In some embodiments, the dichroic beamsplitter includes a dichroic coating that is tuned to reflect a portion of the light energy emitted by the light source so that between 99% and 0.01% is reflected.

In certain embodiments, the dichroic beamsplitter is configured to reflect a portion of the light energy emitted by the light source as an imaging beam.

In various embodiments, the imaging beam is directed toward a detector for analysis of the light energy reflected from at least one of the light guides.

In some embodiments, the optical alignment system further includes an illuminator that illuminates the at least one of the guide proximal ends to provide improved image quality and brightness.

In certain embodiments, the system controller controls the illuminator and adjusts an image brightness and contrast.

In various embodiments, wherein the optical alignment system further includes one of a stepper motor and a piezo actuator that is configured to adjust the yaw, pitch, and roll of at least one of the light guides.

In some embodiments, wherein the optical alignment system further includes optical compensators that are configured to adjust the positioning of the light source relative to the at least one of the guide proximal ends.

In certain embodiments, the optical compensators include a plurality of optical steering wedges positioned in the path of the light source, the plurality of optical steering wedges being configured to improve the coupling of the light source, and the at least one of the guide proximal ends.

The present invention is also directed toward a method for treating a vascular lesion within or adjacent to a vessel wall within a body of a patient using the catheter system of any of the embodiments described herein.

The present invention is further directed toward a method for manufacturing the catheter system of any of the embodiments described herein.

The present invention is also directed toward a method for treating a treatment site within or adjacent to a vessel wall or a heart valve using a catheter system. In various embodiments, the method can include the steps of generating light energy using a light source, directing the light energy toward at least one of a guide proximal end of a first light guide and a guide proximal end of a second light guide, determining an alignment of the light energy relative to at least one of the guide proximal ends of the light guides with an optical alignment system, and adjusting a positioning of the light energy relative to the at least one of the guide proximal ends of the light guides with the optical alignment system based on the alignment of the light energy.

In some embodiments, the optical alignment system is configured to improve optical coupling between the light energy and the at least one of the guide proximal ends of the light guides.

In certain embodiments, the optical alignment system further includes an image sensor that senses the alignment between the light energy and to the at least one of the guide proximal ends of the light guides, the image sensor being configured to provide a visualization of the alignment.

In various embodiments, the method can further include the step of configuring a system controller that is configured to control the optical alignment system so that the light energy is substantially coupled to the at least one of the guide proximal ends of the light guides.

In some embodiments, at least one of the light guides is an optical fiber.

In certain embodiments, the light source is a laser.

In various embodiments, the optical alignment system further includes an optical aligner that is configured to align the light energy with the at least one of the guide proximal ends of the light guides.

In some embodiments, the optical aligner is controlled by the system controller.

In certain embodiments, the optical alignment system further includes an imaging system including an imaging sensor, the imaging system being configured to capture images of a focal point of the light source.

In various embodiments, the imaging system is configured to simultaneously capture images of the focal point of the light source and a scattered energy beam scattered off the at least one of the guide proximal ends of the light guides.

In some embodiments, the imaging system is configured to utilize an image reference frame that allows direct computation of distance offset from the center of the at least one of the guide proximal ends of the light guides.

In certain embodiments, the imaging system is configured to determine the offset and compute compensation adjustment of the alignment of the light energy and the at least one of the guide proximal ends of the light guides.

In various embodiments, the method can further include the step of configuring a system controller that is configured to control an optics mover that positions the multiplexer and aligns the source and the at least one of the guide proximal ends of the light guides.

In some embodiments, the method can further include the step of coupling a light source mover to the multiplexer, the light source mover being connected to the optics mover so that the optics mover can position the multiplexer along the light source mover.

In certain embodiments, the system controller is configured to align the light source into one of (i) a third light guide that receives the light energy from the light source, the third light guide having a guide proximal end, and (ii) a third light guide that receives the light energy from the light source, the third light guide having a guide proximal end.

In various embodiments, the light source is a pulsed IR laser.

In some embodiments, the multiplexer further includes optical elements including a dichroic beamsplitter that splits the light source into at least two guide beams.

In certain embodiments, the dichroic beamsplitter is configured to reflect a reflected light energy with a shorter wavelength than the light energy emitted by the light source.

In various embodiments, the dichroic beamsplitter includes a dichroic coating that is tuned to reflect a portion of the light energy emitted by the light source so that between 99% and 0.01% is reflected.

In some embodiments, the dichroic beamsplitter is configured to reflect a portion of the light energy emitted the at least one of the guide proximal ends of the light guides as an imaging beam.

In certain embodiments, the method can further include the step of directing the light energy reflected from the at least one of the guide proximal ends of the light guides toward a detector for analysis.

In various embodiments, the optical alignment system further includes an illuminator that illuminates the at least one of the guide proximal ends of the light guides to provide improved image quality and brightness.

In some embodiments, the system controller controls the illuminator and adjusts an image brightness and contrast.

In certain embodiments, the optical alignment system further includes one of a stepper motor and a piezo actuator that is configured to adjust the yaw, pitch, and roll of at least one of the light guides.

In various embodiments, the optical alignment system further includes optical compensators that are configured to adjust the positioning of the individual guide beam relative to at least one of the light guides.

In some embodiments, the optical compensators include a plurality of optical steering wedges positioned in the path of the light source, the plurality of optical steering wedges being configured to improve the coupling of the light source, and the at least one of the guide proximal ends of the light guides.

In certain embodiments, the optical alignment system further includes a reflector and a reflector mover that moves the reflector.

The present invention is also directed toward a method for treating a treatment site within or adjacent to a vessel wall or a heart valve using a catheter system. In various embodiments, the method can include the steps of determining an alignment of a light energy relative to at least one of a guide proximal ends of a first light guide and a guide proximal end of a second light guide with an optical alignment system, and adjusting a positioning of the light energy relative to the at least one of the guide proximal ends of the light guides with the optical alignment system based on the alignment of the light energy.

The present invention is directed toward a catheter system for treating a treatment site within or adjacent to a vessel wall or a heart valve. In various embodiments, the catheter system includes a light source, a first light guide, a second light guide, and a light source mover. The light source generates light energy. The first light guide receives the light energy from the light source, the first light guide having a guide proximal end. The second light guide that receives the light energy from the light source, the second light guide having a guide proximal end. An optical alignment system determines an alignment of the light energy relative to at least one of the guide proximal ends, the optical alignment system adjusting the positioning of the light energy relative to the at least one of the guide proximal ends based at least partially on the alignment of the light energy relative to the at least one of the guide proximal ends.

The present invention is also directed toward a method for treating a treatment site within or adjacent to a vessel wall or a heart valve using a catheter system. In various embodiments, the method can include the steps of generating light energy using a light source; receiving light energy into one of a first light guide and a second light guide; moving, using a light source mover, the light source so that the light energy s aligned within a guide proximal end of (i) the first light guide and (ii) the second light guide, and detecting, using the light source mover, the alignment of the light energy relative to the guide proximal end of at least one of the light guides.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which in most cases, similar reference characters refer to similar parts, and in which.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions (also sometimes referred to herein as "treatment sites") can reduce major adverse events or death in affected subjects. As referred to herein, a major adverse event is one that can occur anywhere within the body due to the presence of a vascular lesion. Major adverse events can include but are not limited to, major adverse cardiac events, major adverse events in the peripheral or central vasculature, major adverse events in the brain, major adverse events in the musculature, or major adverse events in any of the internal organs.

As used herein, the terms "intravascular lesion," "vascular lesion," and "treatment site" are used interchangeably unless otherwise noted. The intravascular lesions and/or the vascular lesions are sometimes referred to herein simply as "lesions." Also, as used herein, the terms "focused location" and "focused spot" can be used interchangeably unless otherwise noted and can refer to any location where the light energy is focused to a small diameter than the initial diameter of the light source.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention, as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

Figure 1:
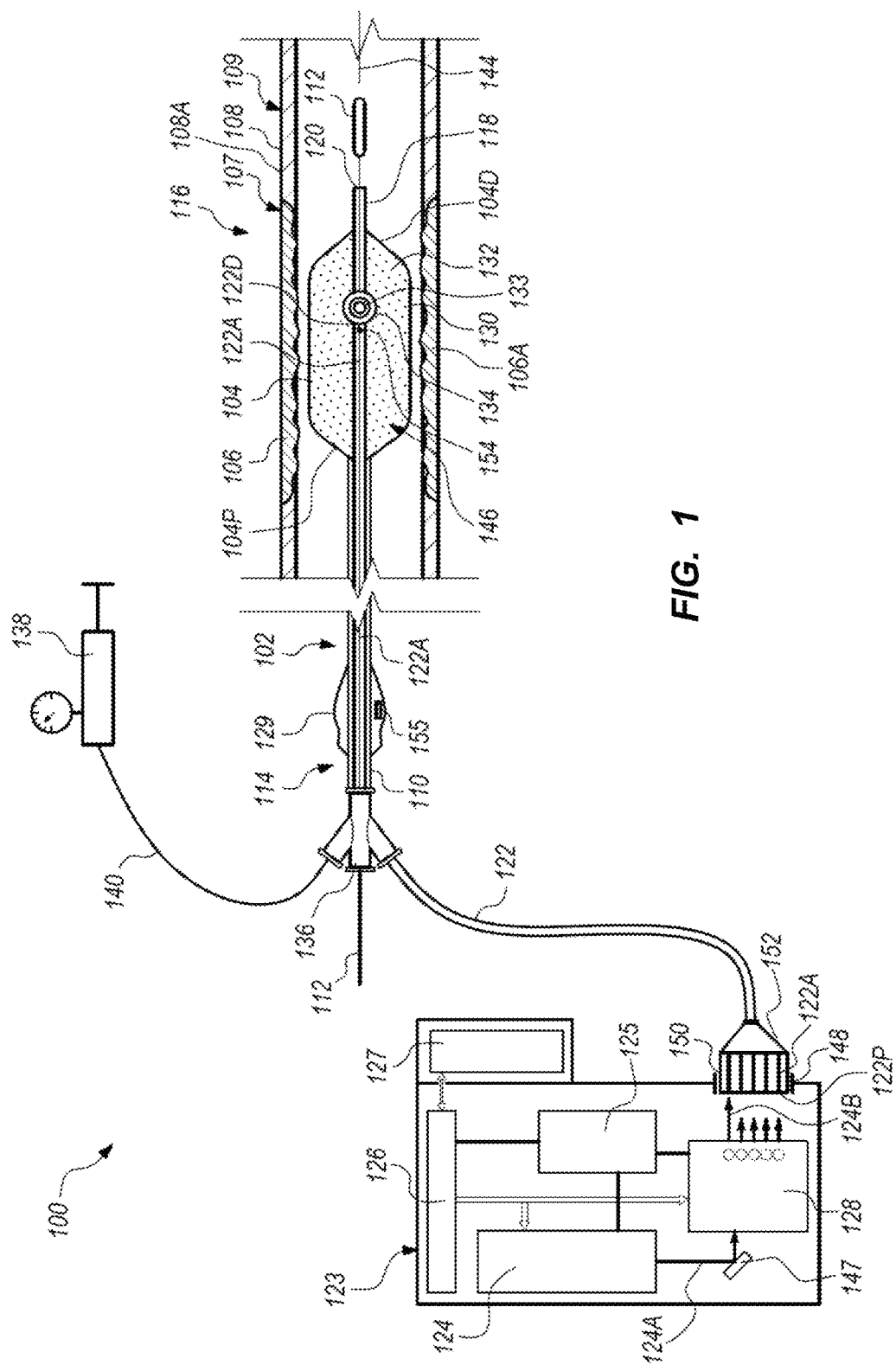
FIG. 1 is a schematic cross-sectional view of an embodiment of a catheter system in accordance with various embodiments herein, the catheter system including a multiplexer having features of the present invention.

The catheter systems disclosed herein can include many different forms. Referring now to FIG. 1, a schematic cross-sectional view is shown of a catheter system 100 in accordance with various embodiments. The catheter system 100 is suitable for imparting pressure waves to induce fractures in one or more treatment sites within or adjacent to a vessel wall of a blood vessel, or on or adjacent to a heart valve, within a body of a patient. In the embodiment illustrated in FIG. 1, the catheter system 100 can include one or more of a catheter 102, a light guide bundle 122 including one or more light guides 122A, a source manifold 136, a fluid pump 138, a multiplexer 123 including one or more of a light source 124, a power source 125, a system controller 126, and a graphic user interface 127 (a "GUI"), a handle assembly 128, and an optical analyzer assembly 142. Alternatively, the catheter system 100 can include more components or fewer components than those specifically illustrated and described in relation to FIG. 1.

It is appreciated that while the catheter system 100 is generally described herein as including a light guide bundle 122 including one or more light guides 122A, and a light source 124, in some alternative embodiments, the catheter system 100 can include an energy guide bundle that includes different types of energy guides, and/or a different type of energy source.

In various embodiments, the catheter 102 is configured to move to a treatment site 106 within or adjacent to a vessel wall 108A of a blood vessel 108 within a body 107 of a patient 109. The treatment site 106 can include one or more vascular lesions 106A, such as calcified vascular lesions, for example. Additionally, or in the alternative, the treatment site 106 can include vascular lesions 106A, such as fibrous vascular lesions. Still alternatively, in some implementations, the catheter 102 can be used at a treatment site 106 within or adjacent to a heart valve within the body 107 of the patient 109.

The catheter 102 can include an inflatable balloon 104 (sometimes referred to herein simply as a "balloon"), a catheter shaft 110, and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118, which is configured to move over the guidewire 112. As utilized herein, the guidewire lumen 118 defines a conduit through which the guidewire 112 extends. The catheter shaft 110 can further include an inflation lumen (not shown) and/or various other lumens for various other purposes. In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The balloon 104 includes a balloon wall 130 that defines a balloon interior 146. The balloon 104 can be selectively inflated with a balloon fluid 132 to expand from a deflated state suitable for advancing the catheter 102 through a patient's vasculature, to an inflated state (as shown in FIG. 1) suitable for anchoring the catheter 102 in position relative to the treatment site 106. Stated in another manner, when the balloon 104 is in the inflated state, the balloon wall 130 of the balloon 104 is configured to be positioned substantially adjacent to the treatment sites 106. It is appreciated that although FIG. 1 illustrates the balloon wall 130 of the balloon 104 is shown spaced apart from the treatment site 106 of the blood vessel 108 when in the inflated state, this is done merely for ease of illustration. It is recognized that the balloon wall 130 of the balloon 104 will typically be substantially directly adjacent to and/or abutting the treatment site 106 when the balloon 104 is in the inflated state.

The balloon 104 suitable for use in the catheter system 100 includes those that can be passed through the vasculature of a patient 109 when in the deflated state. In some embodiments, the balloon 104 is made from silicone. In other embodiments, the balloon 104 can be made from polydimethylsiloxane (PDMS), polyurethane, polymers such as PEBAX™ material, nylon, or any other suitable material.

The balloon 104 can have any suitable diameter (in the inflated state). In various embodiments, the balloon 104 can have a diameter (in the inflated state) ranging from less than one millimeter (mm) up to 25 mm. In some embodiments, the balloon 104 can have a diameter (in the inflated state) ranging from at least 1.5 mm up to 14 mm. In some embodiments, the balloons 104 can have a diameter (in the inflated state) ranging from at least two mm up to five mm.

In some embodiments, the balloon 104 can have a length ranging from at least three mm to 300 mm. More particularly, in some embodiments, the balloon 104 can have a length ranging from at least eight mm to 200 mm. It is appreciated that a balloon 104 having a relatively longer length can be positioned adjacent to larger treatment sites 106, and, thus, may be used for imparting pressure waves onto and inducing fractures in larger vascular lesions 106A or multiple vascular lesions 106A at precise locations within the treatment site 106. It is further appreciated that a longer balloon 104 can also be positioned adjacent to multiple treatment sites 106 at any one given time.

The balloon 104 can be inflated to inflation pressures of between approximately one atmosphere (atm) and 70 atm. In some embodiments, the balloon 104 can be inflated to inflation pressures of from at least 20 atm to 60 atm. In other embodiments, the balloon 104 can be inflated to inflation pressures of from at least six atm to 20 atm. In still other embodiments, the balloon 104 can be inflated to inflation pressures of from at least three atm to 20 atm. In yet other embodiments, the balloon 104 can be inflated to inflation pressures of from at least two atm to ten atm.

The balloon 104 can have various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloon 104 can include a drug-eluting coating or a drug-eluting stent structure. The drug-eluting coating or drug-eluting stent can include one or more therapeutic agents, including anti-inflammatory agents, anti-neoplastic agents, anti-angiogenic agents, and the like.

The balloon fluid 132 can be a liquid or a gas. Some examples of the balloon fluid 132 suitable for use can include, but are not limited to one or more of water, saline, contrast medium, fluorocarbons, perfluorocarbons, gases, such as carbon dioxide, or any other suitable balloon fluid 132. In some embodiments, the balloon fluid 132 can be used as a base inflation fluid. In some embodiments, the balloon fluid 132 can include a mixture of saline to contrast medium in a volume ratio of approximately 50:50. In other embodiments, the balloon fluid 132 can include a mixture of saline to contrast medium in a volume ratio of approximately 25:75. In still other embodiments, the balloon fluid 132 can include a mixture of saline to contrast medium in a volume ratio of approximately 75:25. However, it is understood that any suitable ratio of saline to contrast medium can be used. The balloon fluid 132 can be tailored on the basis of composition, viscosity, and the like so that the rate of travel of the pressure waves are appropriately manipulated. In certain embodiments, the balloon fluid 132 suitable for use herein is biocompatible. A volume of balloon fluid 132 can be tailored by the chosen light source 124 and the type of balloon fluid 132 used.

In some embodiments, the contrast agents used in the contrast media can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as perfluorocarbon dodecafluoropentane (DDFP, C5F12).

The balloon fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 µm) of the electromagnetic spectrum. Suitable absorptive agents can include those with absorption maxima along the spectrum from at least ten nm to 2.5 µm. Alternatively, the balloon fluid 132 can include absorptive agents that can selectively absorb light in the mid-infrared region (e.g., at least 2.5 µm to 15 µm), or the far-infrared region (e.g., at least 15 µm to one mm) of the electromagnetic spectrum. In various embodiments, the absorptive agent can be those that have an absorption maximum matched with the emission maximum of the laser used in the catheter system 100. By way of non-limiting examples, various lasers described herein can include neodymium:yttrium-aluminum-garnet (Nd:YAG–emission maximum=1064 nm) lasers, holmium:YAG (Ho:YAG–emission maximum=2.1 µm) lasers, or erbium:YAG (Er:YAG–emission maximum=2.94 µm) lasers. In some embodiments, the absorptive agents can be water-soluble. In other embodiments, the absorptive agents are not water-soluble. In some embodiments, the absorptive agents used in the balloon fluids 132 can be tailored to match the peak emission of the light source 124. Various light sources 124 having emission wavelengths of at least ten nanometers to one millimeter are discussed elsewhere herein.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the balloon 104. Each of the light guides 122A can have a guide distal end 122D that is at any suitable longitudinal position relative to a length of the balloon 104. In some embodiments, each light guide 122A can be an optical fiber, and the light source 124 can be a laser. The light source 124 can be in optical communication with the light guides 122A at the proximal portion 114 of the catheter system 100. More particularly, the light source 124 can selectively, simultaneously, sequentially, and/or alternatively be in optical communication with each of the light guides 122A in any desired combination, order, and/or pattern due to the presence and operation of the multiplexer 128.

In some embodiments, the catheter shaft 110 can be coupled to multiple light guides 122A, such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110; or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, the light guides 122A can be disposed either uniformly or non-uniformly about the guidewire lumen 118 and/or the catheter shaft 110 to achieve the desired effect in the desired locations.

The catheter system 100 and/or the light guide bundle 122 can include any number of light guides 122A in optical communication with the light source 124 at the proximal portion 114, and with the balloon fluid 132 within the balloon interior 146 of the balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than 30 light guides 122A.

The light guides 122A can have any suitable design for purposes of generating plasma and/or pressure waves in the balloon fluid 132 within the balloon interior 146. In certain embodiments, the light guides 122A can include an optical fiber or flexible light pipe. The light guides 122A can be thin and flexible and can allow light signals to be sent with very little loss of strength. The light guides 122A can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide light energy along its length from a guide proximal end 122P to the guide distal end 122D having at least one optical window (not shown) that is positioned within the balloon interior 146.

In various embodiments, the guide distal end 122D can further include and/or incorporate a distal light receiver 122R that enables light energy to be moved back into and through the light guide 122A from the guide distal end 122D to the guide proximal end 122P. Stated another way, the light energy can move in a first direction 121F along the light guide 122A that is generally from the guide proximal end 122P toward the guide distal end 122D of the light guide 122A. At least a portion of the light energy can also move in a second direction 121S along the light guide 122A that is substantially opposite the first direction 121F, i.e., from the guide distal end 122D toward the guide proximal end 122P of the light guide 122A. Moreover, as described in greater detail herein below, the light energy emitted from the guide proximal end 122P after being moved back through the light guide 122A (in the second direction 121S) can be separated and then optically detected, interrogated, and/or analyzed through use of the optical analyzer assembly 142.

The light guides 122A can assume many configurations about and/or relative to the catheter shaft 110 of the catheter 102. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A can be disposed within one or more light guide lumens within the catheter shaft 110.

The light guides 122A can also be disposed at any suitable positions about the circumference of the guidewire lumen 118 and/or the catheter shaft 110, and the guide distal end 122D of each of the light guides 122A can be disposed at any suitable longitudinal position relative to the length of the balloon 104 and/or relative to the length of the guidewire lumen 118 to more effectively and precisely impart pressure waves for purposes of disrupting the vascular lesions 106A at the treatment site 106.

In certain embodiments, the light guides 122A can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. Additionally, in such embodiments, the photoacoustic transducers 154 can have a shape that corresponds with and/or conforms to the guide distal end 122D of the light guide 122A.

The photoacoustic transducer 154 is configured to convert light energy into an acoustic wave at or near the guide distal end 122D of the light guide 122A. The direction of the acoustic wave can be tailored by changing an angle of the guide distal end 122D of the light guide 122A.

In certain embodiments, the photoacoustic transducers 154 disposed at the guide distal end 122D of the light guide 122A can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. The light guide 122A can further include additional photoacoustic transducers 154 disposed along one or more side surfaces of the length of the light guide 122A.

In some embodiments, the light guides 122A can further include one or more diverting features or "diverters" (not shown in FIG. 1) within the light guide 122A that are configured to direct light to exit the light guide 122A toward a side surface which can be located at or near the guide distal end 122D of the light guide 122A, and toward the balloon wall 130. A diverting feature can include any feature of the system that diverts light energy from the light guide 122A away from its axial path toward a side surface of the light guide 122A. Additionally, the light guides 122A can each include one or more light windows disposed along the longitudinal or circumferential surfaces of each light guide 122A and in optical communication with a diverting feature. Stated in another manner, the diverting features can be configured to direct light energy in the light guide 122A toward a side surface that is at or near the guide distal end 122D, where the side surface is in optical communication with a light window. The light windows can include a portion of the light guide 122A that allows light energy to exit the light guide 122A from within the light guide 122A, such as a portion of the light guide 122A lacking a cladding material on or about the light guide 122A.

Examples of the diverting features suitable for use include a reflecting element, a refracting element, and a fiber diffuser. The diverting features suitable for focusing light energy away from the tip of the light guides 122A can include, but are not to be limited to, those having a convex surface, a gradient-index (GRIN) lens, and a mirror focus lens. Upon contact with the diverting feature, the light energy is diverted within the light guide 122A to one or more of a plasma generator 133 and the photoacoustic transducer 154 that is in optical communication with a side surface of the light guide 122A. As noted, the photoacoustic transducer 154 then converts light energy into an acoustic wave that extends away from the side surface of the light guide 122A.

The source manifold 136 can be positioned at or near the proximal portion 114 of the catheter system 100. The source manifold 136 can include one or more proximal end openings that can receive the one or more light guides 122A of the light guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132 as needed.

As noted above, in the embodiment illustrated in FIG. 1, the multiplexer 123 includes one or more of the light source 124, the power source 125, the system controller 126, and the GUI 127. Alternatively, the multiplexer 123 can include more components or fewer components than those specifically illustrated in FIG. 1. For example, in certain non-exclusive alternative embodiments, the multiplexer 123 can be designed without the GUI 127. Still alternatively, one or more of the light source 124, the power source 125, the system controller 126, and the GUI 127 can be provided within the catheter system 100 without the specific need for the multiplexer 123.

In some embodiments, the multiplexer 123 can include a two-channel splitter design. The guide bundle 122 can include a manual positioning mechanism that is mounted on an optical breadboard and/or platen. This design enables linear positional adjustment and array tilting by rotating about a channel one light guide 122A axis (not shown in FIG. 1). The adjustment method, in other embodiments, can two adjustment steps, 1) aligning the planar positions of the source beam 124B at Channel 1, and 2) adjusting the light guide bundle 122 to achieve the best alignment at Channel 10.

As illustrated in FIG. 1, in certain embodiments, at least a portion of the optical analyzer assembly 142 can also be positioned substantially within the multiplexer 123. Alternatively, components of the optical analyzer assembly 142 can be positioned in a different manner than what is specifically shown in FIG. 1.

As shown, the multiplexer 123, and the components included therewith, is operatively coupled to the catheter 102, the light guide bundle 122, and the remainder of the catheter system 100. For example, in some embodiments, as illustrated in FIG. 1, the multiplexer 123 can include a console connection aperture 148 (also sometimes referred to generally as a "socket") by which the light guide bundle 122 is mechanically coupled to the multiplexer 123. In such embodiments, the light guide bundle 122 can include a guide coupling housing 150 (also sometimes referred to generally as a "ferrule") that houses a portion, e.g., the guide proximal end 122P, of each of the light guides 122A. The guide coupling housing 150 is configured to fit and be selectively retained within the console connection aperture 148 to provide the mechanical coupling between the light guide bundle 122 and the multiplexer 123.

The light guide bundle 122 can also include a guide bundler 152 (or "shell") that brings each of the individual light guides 122A closer together so that the light guides 122A and/or the light guide bundle 122 can be in a more compact form as it extends with the catheter 102 into the blood vessel 108 during use of the catheter system 100. In some embodiments, the light guides 122A leading to the plasma generator 133 can be organized into a light guide bundle 122, including a linear block with an array of precision holes forming a multi-channel ferrule. In other embodiments, the light guide bundle 122 could include a mechanical connector array or block connector that organizes singular ferrule into a linear array The light source 124 can be selectively and/or alternatively coupled in optical communication with each of the light guides 122A, i.e., to the guide proximal end 122P of each of the light guides 122A, in the light guide bundle 122. In particular, the light source 124 is configured to generate light energy in the form of a source beam 124A, such as a pulsed source beam, that can be selectively and/or alternatively directed to and received by each of the light guides 122A in the light guide bundle 122 as an individual guide beam 124B. Alternatively, the catheter system 100 can include more than one light source 124. For example, in one non-exclusive alternative embodiment, the catheter system 100 can include a separate light source 124 for each of the light guides 122A in the light guide bundle 122. The light source 124 can be operated at low energies.

The light source 124 can have any suitable design. In certain embodiments, the light source 124 can be configured to provide sub-millisecond pulses of light energy from the light source 124 that are focused onto a small spot in order to couple it into the guide proximal end 122P of the light guide 122A. Such pulses of light energy are then directed and/or guided along the light guides 122A to a location within the balloon interior 146 of the balloon 104, thereby inducing plasma formation (also sometimes referred to herein as a "plasma flash") in the balloon fluid 132 within the balloon interior 146 of the balloon 104, such as via the plasma generator 133 that can be located at the guide distal end 122D of the light guide 122A. In particular, the light emitted at the guide distal end 122D of the light guide 122A energizes the plasma generator 133 to form the plasma within the balloon fluid 132 within the balloon interior 146. The plasma formation causes rapid bubble formation and imparts pressure waves upon the treatment site 106. An exemplary plasma-induced bubble 134 is illustrated in FIG. 1.

When the plasma initially forms in the balloon fluid 132 within the balloon interior 146, it emits broad-spectrum electromagnetic radiation. This can be seen as a flash of broad-spectrum light detectable by the naked eye. A portion of the light emitted from the plasma bubble 134 can be coupled into the distal light receiver 122R at the guide distal end 122D of the light guide 122A and travel back to the guide proximal end 122P, where it can be separated, detected, and analyzed through use of the optical analyzer assembly 142. The intensity and timing of the visible light pulse relative to the plasma generating pulse provides an indication that the plasma generator 133 functioned, its energy output, and its functional condition. Visible light flashes may occur in other locations of the light guide 122A if the light guide 122A is damaged or broken. Such other visible light flashes will also be coupled into the light guide 122A and carried back to the guide proximal end 122P. The intensity and timing of these other light pulses provide an indication of damage to or failure of the light guide 122A or the plasma generator 133. In such situations, the optical analyzer assembly 142 can include a safety shutdown system 283 (illustrated in FIG. 2A) that can be selectively activated to shut down operation of the catheter system 100.

The configuration of the plasma generator 133 and/or the distal light receiver 122R further allows ambient light that originates outside of the catheter 102 to be coupled into the guide distal end 122D of the light guide 122A. In one implementation, the optical analyzer assembly 142 monitors for returned ambient light energy that traverses the light guide 122A from the guide distal end 122D to the guide proximal end 122P. If any ambient light energy is present and detected by the optical analyzer assembly 142 in such situations, this is an indication that the catheter 102 is located outside of the body 107 of the patient 109, and the optical analyzer assembly 142 can be configured to lock out the light source 124 accordingly. In particular, in such situations, the safety shutdown system 283 of the optical analyzer assembly 142 can be selectively activated to shut down operation of the catheter system 100.

In various non-exclusive alternative embodiments, the sub-millisecond pulses of light energy from the light source 124 can be delivered to the treatment site 106 at a frequency of between approximately one hertz (Hz) and 5000 Hz, between approximately 30 Hz and 1000 Hz, between approximately ten Hz and 100 Hz, or between approximately one Hz and 30 Hz. Alternatively, the sub-millisecond pulses of light energy can be delivered to the treatment site 106 at a frequency that can be greater than 5000 Hz or less than one Hz, or any other suitable range of frequencies.

It is appreciated that although the light source 124 is typically utilized to provide pulses of light energy, the light source 124 can still be described as providing a single source beam 124A, i.e., a single pulsed source beam.

The light sources 124 suitable for use can include various types of light sources, including lasers and lamps. For example, in certain non-exclusive embodiments, the light source 124 can be an infrared laser that emits light energy in the form of pulses of infrared light. Alternatively, as noted above, the light sources 124, as referred to herein, can include any suitable type of energy source.

Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths, and energy levels that can be employed to achieve plasma in the balloon fluid 132 of the catheter 102. In various non-exclusive alternative embodiments, the pulse widths can include those falling within a range including from at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the light sources 124 suitable for use in the catheter system 100 can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers ($\mu$m). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter system 100 can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In various non-exclusive alternative embodiments, the catheter system 100 can generate pressure waves having maximum pressures in the range of at least approximately two MPa to 50 MPa, at least approximately two MPa to 30 MPa, or at least approximately 15 MPa to 25 MPa.

The pressure waves can be imparted upon the treatment site 106 from a distance within a range from at least approximately 0.1 millimeters (mm) to greater than approximately 25 mm, extending radially from the light guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the light guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide the necessary power to each of the light source 124, the system controller 126, the GUI 127, the handle assembly 128, and the optical analyzer assembly 142. The power source 125 can have any suitable design for such purposes.

The system controller 126 is electrically coupled to and receives power from the power source 125. Additionally, the system controller 126 is coupled to and is configured to control operation of each of the light source 124, the GUI 127, and the optical analyzer assembly 142. The system controller 126 can include one or more processors or circuits for purposes of controlling the operation of at least the light source 124, the GUI 127, and the optical analyzer assembly 142. For example, the system controller 126 can control the light source 124 for generating pulses of light energy as desired and/or at any desired firing rate. Additionally, the system controller 126 can control and/or operate in conjunction with the optical analyzer assembly 142 to effectively provide continuous real-time monitoring of the performance, reliability, safety, and proper usage of the catheter system 100.

The system controller 126 can further be configured to control operation of other components of the catheter system 100 such as the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. Additionally, the GUI 127 is electrically connected to the system controller 126. With such design, the GUI 127 can be used by the user or operator to ensure that the catheter system 100 is effectively utilized to impart pressure onto and induce fractures at the treatment site(s) 106. The GUI 127 can provide the user or operator with information that can be used before, during, and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time during use of the catheter system 100. In various embodiments, the GUI 127 can include one or more colors, different sizes, varying brightness, etc., that may act as alerts to the user or operator. Additionally, or in the alternative, the GUI 127 can provide audio data or information to the user or operator. The specifics of the GUI 127 can vary depending upon the design requirements of the catheter system 100, or the specific needs, specifications, and/or desires of the user or operator.

As shown in FIG. 1, the handle assembly 128 can be positioned at or near the proximal portion 114 of the catheter system 100, and/or near the source manifold 136. In this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position, and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the light source 124, the fluid pump 138, the GUI 127, and the optical analyzer assembly 142. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. In some embodiments, the circuitry 156 can receive electrical signals or data from the optical analyzer assembly 142. Further, or in the alternative, the circuitry 156 can transmit such electrical signals or otherwise provide data to the system controller 126.

In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, e.g., within the multiplexer 123. It is understood that the handle assembly 128 can include fewer or additional components than those specifically illustrated and described herein.

Figure 2:
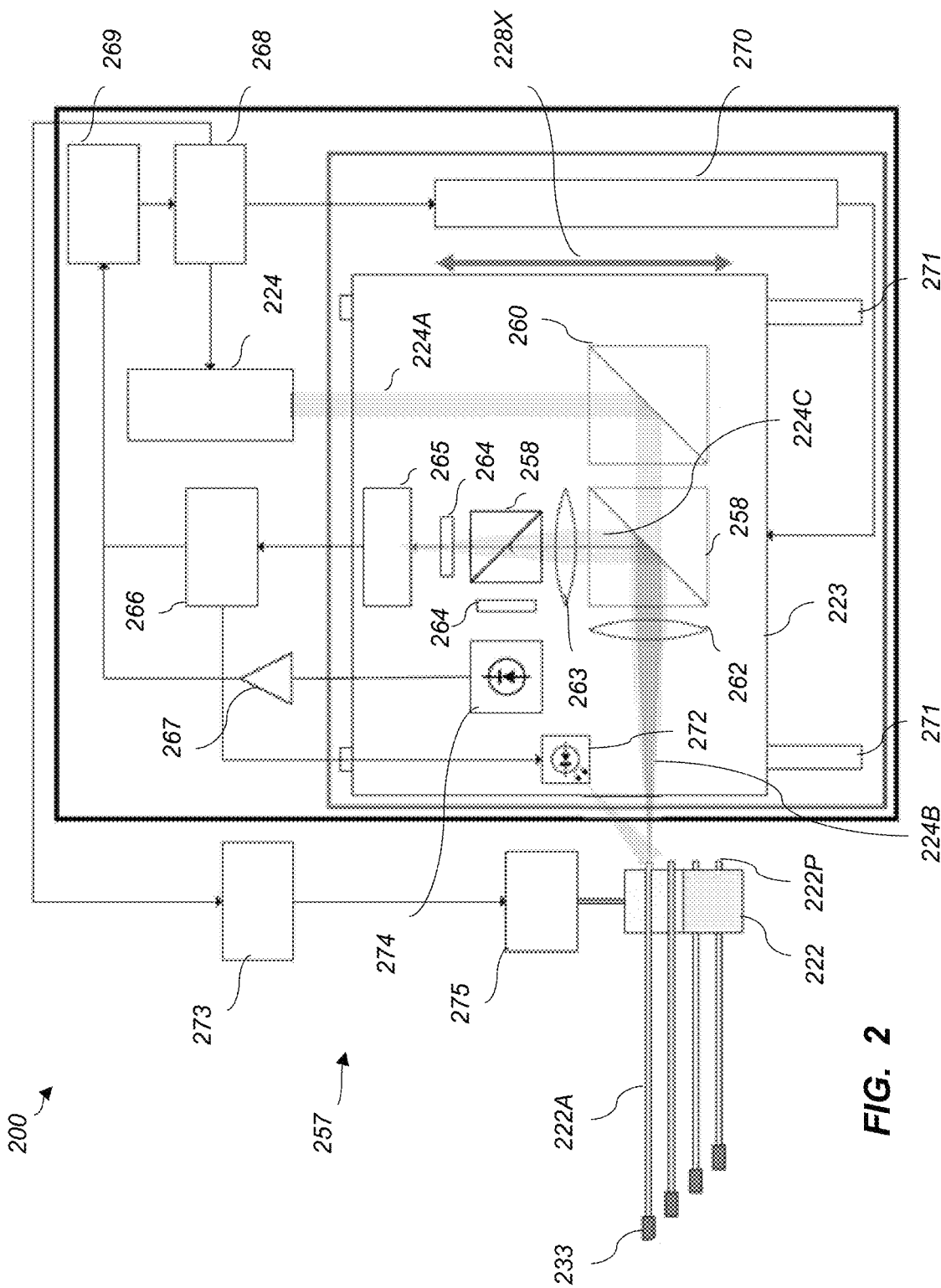
FIG. 2 is a simplified schematic view of a portion of an embodiment of the catheter system, including an embodiment of an optical alignment system, the optical alignment system being utilized in a first alignment configuration.

FIG. 2 is a simplified schematic view of a portion of an embodiment of the catheter system 200, including an embodiment of the optical alignment system 257, the optical alignment system 257 being utilized in a first alignment configuration.

The design of the catheter system 200 is substantially similar to the embodiments illustrated and described herein. It is appreciated that various components of the catheter system 200, such as are shown in FIG. 1, are not illustrated in FIG. 2 for purposes of clarity and ease of illustration. However, it is appreciated that the catheter system 200 can include most, if not all, of such components. Additionally, in some embodiments, the components of the catheter system 200 can be mounted and/or fixed on platens.

As shown in FIG. 2, the catheter system 200 again includes a light source 224 that is configured to generate light energy in the form of a source beam 224A, e.g., a pulsed source beam, that can be selectively and/or alternatively directed to and received by each light guide 222A (within the light guide bundle 222) as an individual guide beam 224B (illustrated in FIG. 2A). In one non-exclusive embodiment, the light source 224 is an infrared laser source, and the light guide 222A is a small diameter, multimode optical fiber.

In certain embodiments, as shown in FIG. 2, the source beam 224A from the light source 224 passes through at least one optical element, including but not limited to one or more beamsplitters 258 (two beamsplitters 258 are illustrated in FIG. 2), one or more reflectors 260 (one reflector 260 is illustrated in FIG. 2), one or more coupling lenses 262 (one coupling lens 262 is illustrated in FIG. 2), one or more imaging lenses 263 (one imaging lens 263 is illustrated in FIG. 2), and/or one or more filters 264 (two filters 264 are illustrated in FIG. 2). Each optical element can be configured to focus, reflect, and/or filter the source beam 224A as the individual guide beam 224B down onto a guide proximal end 222P of the light guide 222A, thereby coupling the individual guide beam 224B in the form of the pulse of infrared energy into the light guide 222A. The individual guide beam 224B, when aligned with the light guide 222A, travels toward the plasma generator 233. In some embodiments, each optical element can be configured to focus, reflect, and/or filter an imaging beam 224C toward a camera 265.

The light energy of the individual guide beam 224B is guided along the light guide 222A from the guide proximal end 222P to the guide distal end 222D and energizes the plasma generator 233 that is positioned and/or incorporated at or near a guide distal end 222D of the light guide 222A. The plasma generator 233 utilizes the pulse of infrared energy to create a localized plasma in the balloon fluid 132 within the balloon interior 146 of the balloon 104.

Figure 3:
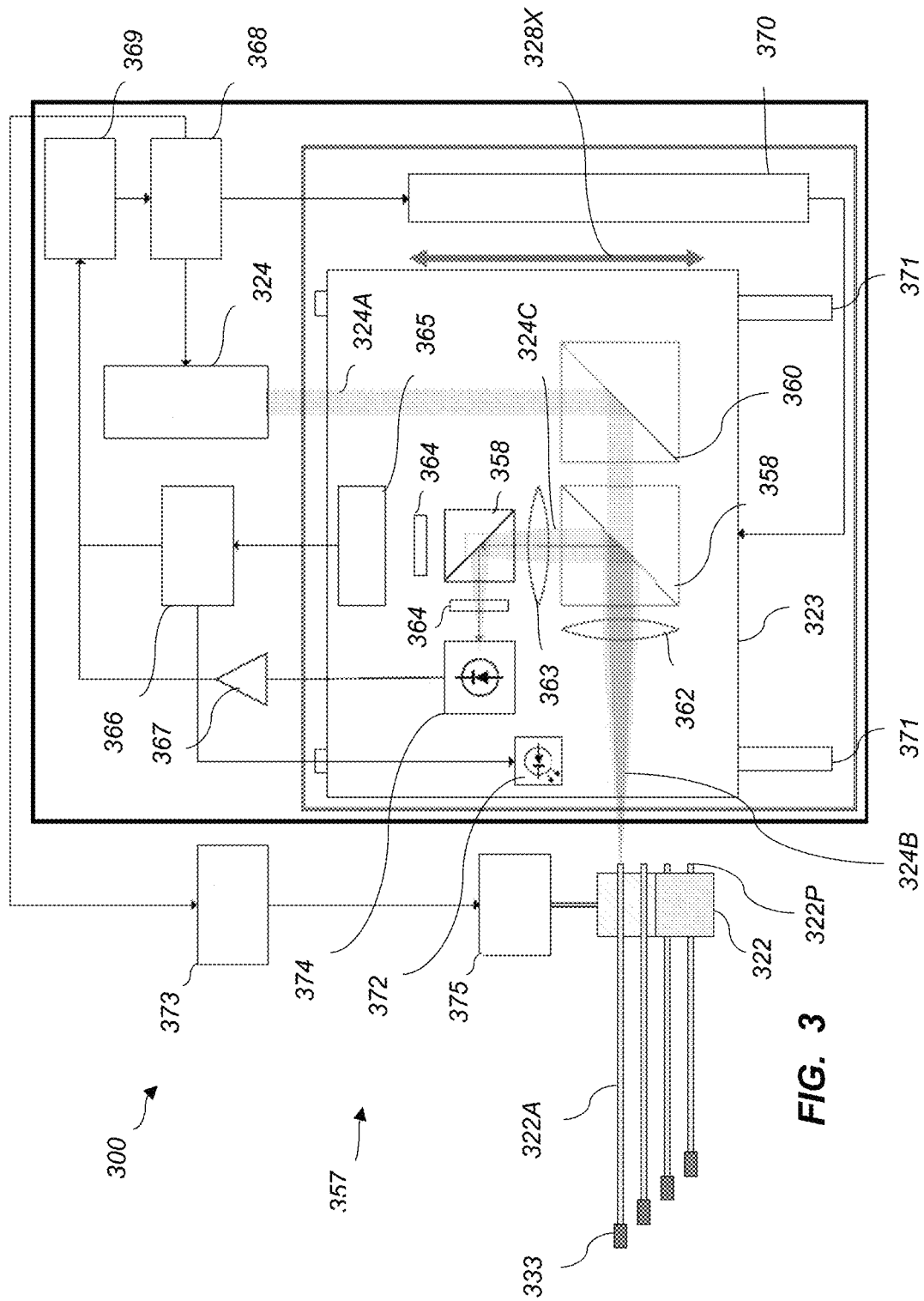
FIG. 3 is a simplified schematic view of a portion of an embodiment of the catheter system, including an embodiment of the optical alignment system, the optical alignment system being utilized in a second alignment configuration.
Figure 4:
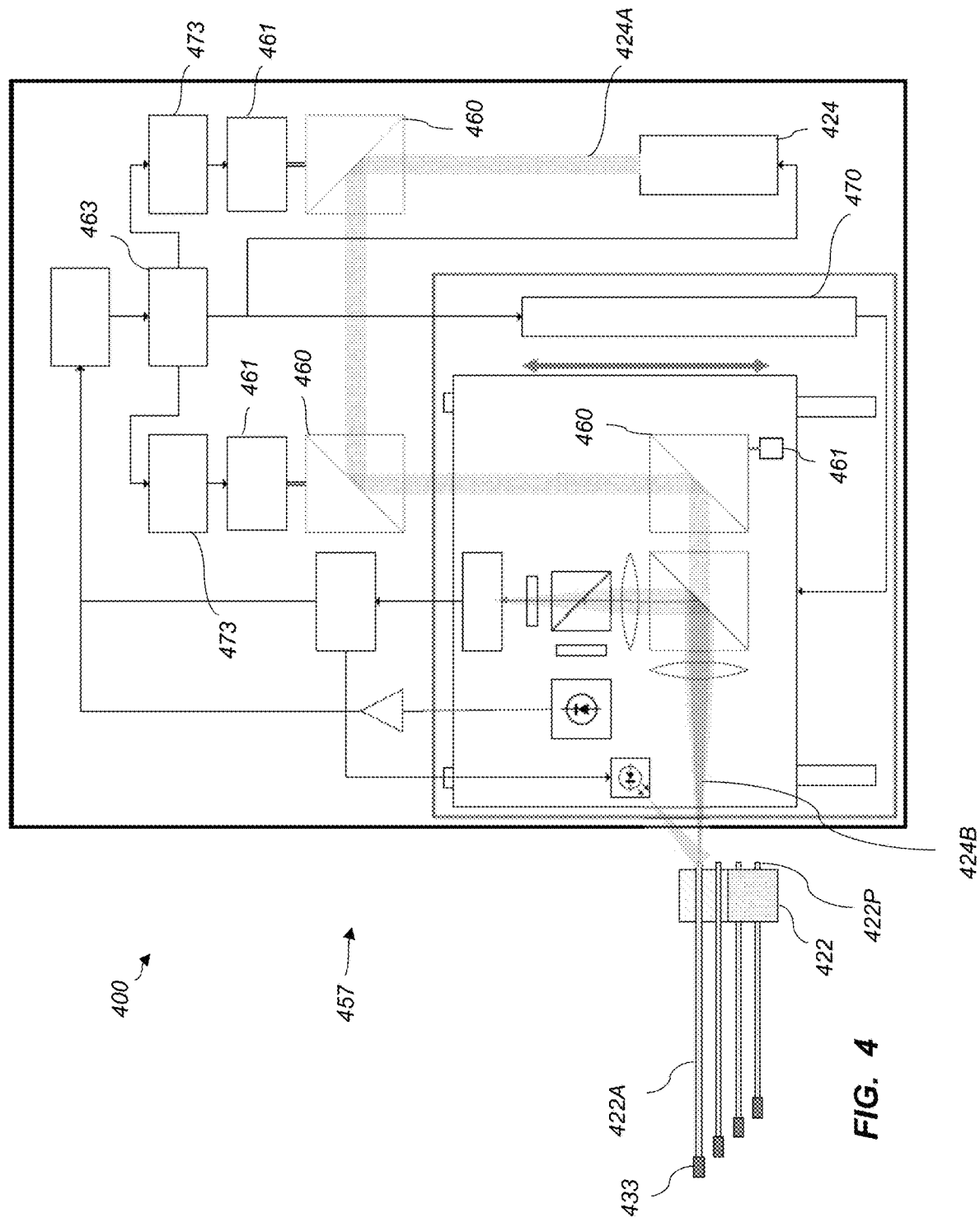
FIG. 4 is a simplified schematic view of a portion of an embodiment of the catheter system, including an embodiment of the optical alignment system, the optical alignment system being utilized in a third alignment configuration.

The optical alignment system 257 can include any and/or all of the components shown in the embodiment illustrated in FIG. 2, FIG. 3, and FIG. 4. The optical alignment system 257 aligns the light energy in the form of the source beam 224A and/or the individual guide beam 224B so that the light energy is coupled with one or more light guides 222A.

The optical alignment system 257 can vary depending on the design requirements of the catheter system 200, the light guides 222A, and/or the energy source 224. It is understood that the optical alignment system 257 can include additional systems, subsystems, components, and elements than those specifically shown and/or described herein. Additionally, or alternatively, the optical alignment system 257 can omit one or more of the systems, subsystems, and elements that are specifically shown and/or described herein.

In various embodiments, the optical alignment system 257 can include a multiplexer 223. The optical elements described herein can be included within a multiplexer 223 (such as the multiplexer 128 described in relation to FIG. 1). As displayed in the embodiment shown in FIG. 2, the multiplexer 223 can be movable about a multiplexer axis 223X. In some embodiments, the multiplexer 223 can be fixed or mounted to a multiplexer platen.

In some embodiments, the optical alignment system 257 can include one or more of the beamsplitter(s) 258, the reflector(s) 260, the coupling lens(es) 262, the imaging lens(es) 263, the filter(s) 264, a camera 265, a camera controller 266, an amplifier 267, a system controller 268, a signal processor 269, an optics mover 270, a light source mover 271, an illuminator 272, an alignment controller 273, a detector 274, and/or an aligner 275.

The beamsplitter 258, such as a dichroic beamsplitter in one embodiment, can be positioned in the optical path of the source beam 224A between the light source 224 and the guide proximal end 222P of the light guide 222A. In certain embodiments, the beam splitter 258 is configured to pass light for wavelengths longer than those visible to the other optical elements of the optical alignment system 257 so that the individual guide beam 224B that is directed toward the guide proximal end 222P of the light guide 222A. Such threshold wavelength can be referred to as the cutoff wavelength. The beamsplitter 258 can be further configured to reflect all light having a wavelength that is shorter than the cutoff wavelength. In some embodiments, the cutoff wavelength can be 950 nm. The dichroic beamsplitter 258 can reflect a small percentage of light energy depending on the ratio of dichroic coating on the beamsplitter 258.

In some embodiments, other optical elements (e.g., the coupling lens 262) can be positioned between one or more of the beamsplitters 258 and the light guide 222A. The beam splitter 258 can be configured to focus the individual guide beam 224B down onto the guide proximal end 222P of the light guide 222A, thereby coupling the individual guide beam 224B into the light guide 222A. One or more of the beamsplitters 258 can be used in combination with other optical elements, such as the imaging lens 263 and the filter 264, in order to focus the imaging beam 224C into the camera 265.

In other embodiments, one or more of the beamsplitters 258 can be positioned in the path of the imaging beam 224C to allow a percentage of the imaging beam 224C to be directed to the detector 274 for analysis of light energy returning through the light guide 222A or the face of the guide proximal end 222P. This photo-analysis can be used for diagnostics and for failure detection methods.

The beamsplitter(s) 258 can vary depending on the design requirements of the catheter system 200, the light guides 222A, and/or the optical alignment system 257. It is understood that the beamsplitter 258 can include additional systems, subsystems, components, and elements than those specifically shown and/or described herein.

The reflector(s) 260 can reflect the light energy emitted by the light source 224 to one or more optical elements of the optical alignment system 257. In one embodiment, the reflector(s) 260 can include a mirror. In certain embodiments, one or more of the reflectors 260 can fold the source beam 224A from the light source 224 at an angle of approximately 90 degrees. Alternatively, one or more of the reflectors 260 can fold the source beam 224A from the light source 224 at an angle that is greater or less than 90 degrees. The reflector(s) 260 can direct the source beam 224A through the coupling lens 262 toward one or more light guides 222A. In one embodiment, one or more of the reflectors 260 can be fixed. Alternatively, one or more of the reflectors 260 can be movable, either manually or by one or more optics movers 270, such as by one or more piezoelectric actuators in one non-exclusive embodiment.

The reflector 260 can vary depending on the design requirements of the catheter system 200, the light guides 222A, and/or the optical alignment system 257. It is understood that the reflector 260 can include additional systems, subsystems, components, and elements than those specifically shown and/or described herein.

The coupling lens 262 can couple the individual guide beam 224B onto the guide proximal end 222P of one or more light guides 222A. The coupling lens 262 can focus and/or collimate the source beam 224A into the individual guide beam 224B. The coupling lens 262 can be used to focus the guide beam 224B down to form a spot that will couple into at least one of the light guides 222A. The coupling lens 262 can also collimate light sources (e.g., the light source 224) near the focusing location (see, e.g., the source beam 524B, FIG. 5B), which is set to be near the guide proximal end 222P of the light guide 222A. The light energy from the guide beam 224B is scattered off of the focused spot on the guide proximal end 222P.

In some embodiments, since the source beam 224B and/or the imaging beam 224C can be collimated, a separate set of optics can focus the source beam 224B and/or the imaging beam 224C to form an image. In various embodiments, since the source beam 224B and/or the imaging beam 224C between the coupling lens 262 and the imaging lens 262 is collimated, the separation between the optical elements is not critical to imaging performance. The various light beams disclosed herein can be separated by a distance convenient for arranging optical elements on any given platen. The focal length of the optics controls the magnification of the light guide 222A on the sensor (such as the camera 265). The separation between optics and image sensor allows for focusing of the image generated at the desired plane at the object independent of the location where the energy source is focused.

The coupling lens 262 can vary depending on the design requirements of the catheter system 200, the light guides 222A, and/or the optical alignment system 257. It is understood that the coupling lens 262 can include additional systems, subsystems, components, and elements than those specifically shown and/or described herein. Additionally, or alternatively, the coupling lens 262 can omit one or more of the systems, subsystems, and elements that are specifically shown and/or described herein.

The imaging lens 263 can couple the imaging beam 224C onto the camera 265 or any suitable imaging system of the optical alignment system 257. The imaging lens 263 can vary depending on the design requirements of the catheter system 200, the light guides 222A, and/or the optical alignment system 257. It is understood that the imaging lens 263 can include additional systems, subsystems, components, and elements than those specifically shown and/or described herein.

The filter 264 can filter the light energy from the source beam 224A, the guide beam 224B and/or the imaging beam 224C. The filter 264 can vary depending on the design requirements of the catheter system 200, the light guides 222A, the optical alignment system 257, and/or the camera 265. It is understood that the filter 264 can include additional systems, subsystems, components, and elements than those specifically shown and/or described herein.

The optical elements disclosed in the various embodiments herein can be configured in any position or order. In some embodiments, such as the embodiment illustrated in FIG. 2, can create optical paths for 1) coupling primary IR energy and 2) imaging the end face of the ferrule (e.g., the guide proximal end 222P), and imaging some of the primary energy scattered or reflected at the end face of the ferrule or conveniently collocated target.

The camera 265 can capture images of the light energy in the form of the imaging beam 224C. In the first alignment configuration (as shown in the embodiment displayed in FIG. 2) of the optical alignment system 257, the camera receives the imaging beam 224C that is reflected and/or scattered back from the guide proximal end 222P. This scattered light is captured by the coupling lens 262 and focused by the imaging lens 263 to form an image of the focused spot.

In various embodiments, the image of the focused spot will be superimposed on the image of the guide proximal end 222P in the same image space. An additional filter 264 can be added to reduce the amount of IR signal arriving from the scattered source and to balance the intensity of the focused spot in the image relative to the guide proximal end 222P and light guide 222A.

In certain embodiments, as the multiplexer 223 scans laterally across the guide proximal end 222P of one or more light guides 222A, the camera 265 creates an image of the guide proximal end 222P in the visible spectrum. This could rely on ambient visible light as an illumination source. Alternatively, a separate source such as the illuminator 272 could illuminate the guide proximal end 222P to improve image quality and brightness.

The camera 265 can vary depending on the design requirements of the catheter system 200 and/or the optical alignment system 257. It is understood that the camera 265 can include additional systems, subsystems, components, and elements than those specifically shown and/or described herein.

The camera controller 266 can control the camera 265. The camera controller 266 can also send signals to the signal processor 269. The camera controller 266 can control the illuminator 272 as necessary to adjust image brightness and contrast. The camera controller 266 can vary depending on the design requirements of the catheter system 200, the light guides 222A, the optical alignment system 257, the camera 265, and/or the signal processor 269. It is understood that the camera controller 266 can include additional systems, subsystems, components, and elements than those specifically shown and/or described herein.

The amplifier 267 can amplify various signals sent from components of the optical alignment system 257. As shown in FIG. 2, the signal from the detector 274 can be directed to the amplifier, where the detection of and intensity evaluation of the imaging beam 224C are determined. In particular, in certain embodiments, the signal from the detector 274 is directed toward the amplifier 267, where the signal from the detector 274 is amplified.

The amplifier 267 can vary depending on the design requirements of the catheter system 200, the light guides 222A, the optical alignment system 257, the camera 265, and/or the signal processor 269. It is understood that the amplifier 267 can include additional systems, subsystems, components, and elements than those specifically shown and/or described herein.

The system controller 268 can control any and/or all of the components of the catheter system 200, the multiplexer 223, and/or the optical alignment system 257. In some embodiments, the system controller 268 controls the emission of light energy from the light source 224. In other embodiments, the system controller 268 controls the optics mover 270.

The system controller 268 can vary depending on the design requirements of the catheter system 200, the multiplexer 223, and/or the optical alignment system 257. It is understood that the system controller 268 can include additional systems, subsystems, components, and elements than those specifically shown and/or described herein.

The signal processor 269 can process various signals sent from components of the optical alignment system 257. The signal processor 269 can monitor and record data of the image information and/or other received signals. The signal processor 269 can segment the image to obtain the light guide 222A core/center location and direct the optical alignment system 257 to align the guide beam 224B to the focused spot location in the image space.

In other embodiments, the signal processor 269 can use the scaling of the image and separate calibrations to determine the exact displacement of the actual focal spot relative to the location of the center/core of the light guide 222A for improved coupling. These calibrations can account for all offsets and drifts in the guide beam 224B and the physical location of the aligned light guide 222A due to the mechanical tolerances and stack-ups. The system controller 268 can then use the data to adjust the location of the light guide bundle 222 using the aligner 275. This brings the focused location into perfect alignment with the core/center of the aligned light guide 222A.

The signal processor 269 can vary depending on the design requirements of the catheter system 200, the light guides 222A, the optical alignment system 257, the camera 265, and/or the amplifier 267. It is understood that the signal processor 269 can include additional systems, subsystems, components, and elements than those specifically shown and/or described herein.

The optics mover 270 moves and/or controls moving components of the optical alignment system 257, such as the light source mover 271. The optics mover 270 can vary depending on the design requirements of the catheter system 200, the optical alignment system 257, and/or the light source mover 271. It is understood that the optics mover 270 can include additional systems, subsystems, components, and elements than those specifically shown and/or described herein.

The light source mover 271 can move the light energy, the light source 224, and/or the multiplexer 223 so that the light energy is properly aligned within at least one of the light guides 222A. In some embodiments, the system controller 268 controls the optics mover 270 that is connected to the light source mover that positions the multiplexer 223 and aligns a beam axis (not shown) of the guide beam 224B within one or more of the light guides 222A. Using the embodiments disclosed herein, the optical alignment system 257 can utilize the light source mover 271 to align the energy source 224 with any desired channel within the light guide bundle 222, trigger the energy source 224, and move to the next desired channel within the light guide bundle 222.

The light source mover 271 can vary depending on the design requirements of the catheter system 200, the light guides 222A, the optical alignment system 257, and/or the optics mover 270. It is understood that light source mover 271 can include additional systems, subsystems, components, and elements than those specifically shown and/or described herein.

In some embodiments, the light source mover 271 can include a linear translation stage. The multiplexer 223 can be configured to move across the linear translation stage about the multiplexer axis 223X.

The illuminator 272 can illuminate the guide proximal end 222P so that the alignment of the light energy and the guide proximal end 222P is easier to detect and analyze by the optical alignment system 257. The illuminator 272 can vary depending on the design requirements of the catheter system 200, the light guides 222A, and/or the optical alignment system 257. It is understood that the illuminator 272 can include additional systems, subsystems, components, and elements than those specifically shown and/or described herein. In some embodiments, the illuminator 272 can include a visible light source such as a visible LED.

The alignment controller 273 controls the alignment components of the optical alignment system 257, such as the aligner 275. The alignment controller 273 can vary depending on the design requirements of the catheter system 200, the light guides 222A, the optical alignment system 257, and/or the aligner 275. It is understood that the alignment controller 273 can include additional systems, subsystems, components, and elements than those specifically shown and/or described herein.

The detector 274 can receive the light energy from the imaging beam 224C when the optical alignment system 257 is in a second alignment configuration (shown in FIG. 3). The detector 274 can detect the light energy from the imaging beam 224C and converts the detected light energy to signals. The detector 274 can send the signals to the amplifier 267 to be amplified and sent to the signal processor 269.

The detector 274 can vary depending on the design requirements of the catheter system 200, the optical alignment system 257, the amplifier 267, and/or the signal processor 269. It is understood that the detector 274 can include additional systems, subsystems, components, and elements than those specifically shown and/or described herein.

The aligner 275 can align various components of the alignment system 257, such as the light guide bundle 222 and the light source mover 271. The aligner 275 can vary depending on the design requirements of the catheter system 200, the light guides 222A, the optical alignment system 257, and/or the alignment controller 273. It is understood that the aligner 275 can include additional systems, subsystems, components, and elements than those specifically shown and/or described herein.

In other embodiments, the aligner 275 can include stepper motors, and/or piezo actuators to adjust the height and tilt of the light guide bundle 222. In one alignment process, the optical alignment system 257 would alight the light source mover 271 near a first channel in the light guide bundle 222 (corresponding with one light guide 222A) and capture an image of the guide proximal end 222P and the corresponding light guide 222A with the guide beam 224B focused location.

In certain embodiments, the magnification of the light guide 222A in the image can be controlled so that the image is small relative to the light guide bundle 222 size in the image. The system controller 268 can calculate the offset and adjust movement parameters in at least two directions to align the focused location with the center/core of the light guide 222A. The system controller 268 can align the source beam 224B with the final light guide 222A in the linear array of the light guide bundle 222 and capture an image of the guide proximal end 222P and the light guide 222A along with the focused location. The positional offset can be used to set the tilt of the light guide bundle 222 by rotating it around the center of one of the light guides 222A. This process could continue iteratively to adjust position and tilt parameters for the light guide 222A as a whole. The process can continue to return to each light guide 222A location and adjust the linear position along the multiplexer axis 223X. This process can be executed as an initial alignment of light source 224 and the optical alignment system 257 to a new guide bundle 222. Once the configuration described herein is completed, the optical alignment system 257 can operate over a time interval during which the alignment would remain stable.

In various embodiments, the optical alignment system 257 would utilize optical compensation devices (e.g., multiple reflectors 260, steering wedges) to adjust the focused location relative to the light guide bundle 222. Steering wedges (not shown) can be placed in the path of the source beam 224A, the guide beam 224B, and/or the imaging beam 224C in order to account for deviations in linear directions within a plane. The optical alignment system 257 can adjust the guide beam 224B location to a pre-aligned light guide bundle 222.

In some embodiments, the image of the focused location could also be obtained from other surfaces or targets than the guide proximal end 222P and/or the light guide 222A. For example, a flat ceramic target could be located near the light guide 222A along a bundle axis of the guide bundle 222. The light source mover 222 could offset the multiplexer 223 a set distance to track the location of the focused location on the new target. The signal processor 269 can subtract the offset when determining the location of the focused location relative to the light guide 222A image space.

In various embodiments, the first alignment configuration can be an initial setup and alignment configuration. In the first alignment configuration, the light guide bundle 222, including the individual light guides 222A, is coupled to the multiplexer 223. The system controller 268 can position the light source mover 271 at the first light guide 222A position. The camera controller 266 can engage the illuminator 272 and begin to capture images of the light guide 222A and the guide proximal end 222P. The system controller 268 can engage pulses of the light source 224 at low energy, and the camera 265 can capture a suitable image. The signal processor 269 can analyze this image and computes the offset to line up linear positional parameters to improve coupling for the first optical channel (e.g., the first light guide 222A in the light guide bundle 222). The optical alignment system 257 can then reiterate the process for each channel in the light guide bundle 222.

FIG. 3 is a simplified schematic view of a portion of an embodiment of the catheter system 300, including an embodiment of the optical alignment system 357, the optical alignment system 357 being utilized in a second alignment configuration.

The design of the catheter system 300 is substantially similar to the embodiments illustrated and described herein. It is appreciated that various components of the catheter system 300, such as are shown in FIG. 1, are not illustrated in FIG. 3 for purposes of clarity and ease of illustration. However, it is appreciated that the catheter system 300 can include most, if not all, of such components.

As shown in FIG. 3, the catheter system 300 again includes a light source 324 that is configured to generate light energy in the form of a source beam 324A, e.g., a pulsed source beam, that can be selectively and/or alternatively directed to and received by each light guide 322A (within the light guide bundle 322) as an individual guide beam 324B. In one non-exclusive embodiment, the light source 324 is an infrared laser source, and the light guide 322A is a small diameter, multimode optical fiber.

In certain embodiments, as shown in FIG. 3, the source beam 324A from the light source 324 passes through at least one optical element, such as one or more beamsplitters 358, one or more reflectors 360, one or more coupling lenses 362, one or more imaging lenses 363, and/or one or more filters 364. Some or all of the optical elements can be configured to focus, reflect, and/or filter the source beam 324A as the individual guide beam 324B down onto a guide proximal end 322P of the light guide 322A, thereby coupling the individual guide beam 324B in the form of the pulse of infrared energy into the light guide 322A. The individual guide beam 324B, when aligned with the light guide 322A, travels toward the plasma generator 333. In some embodiments, each optical element can be configured to focus, reflect, and/or filter an imaging beam 324C toward the camera 365.

As illustrated in the embodiment of FIG. 3, the catheter system 300 can again include the multiplexer 323 having the multiplexer axis 323X, the camera controller 366, the amplifier 367, the system control 368, the signal processor 369, the optics mover 370, the light source mover 371, the illuminator 372, the alignment controller 373, the detector 374, and/or the aligner 375. Each of the components can have the same and/or substantially similar functionality and/or components as described in the embodiments disclosed herein.

In the second alignment configuration (shown in FIG. 3), the detector 374 can receive the light energy from the imaging beam 324C. The detector 374 can detect the light energy from the imaging beam 324C and converts the detected light energy to signals. The detector 374 can send the signals to the amplifier 367 to be amplified and sent to the signal processor 369.

In other embodiments, the second alignment configuration can be a high-energy mode. In the second alignment configuration, the optical alignment system 357 would have already completed the initial setup and alignment process described in the first alignment configuration. In the second alignment configuration, the optical alignment system 357 can the light source mover 371 at a predetermined position along the multiplexer axis 323X for a given optical channel and fire the light source 324. The optical alignment system 357 collects light that is reflected as the imaging beam 324C and directs the imaging beam 324 to the detector 374. The detector 374 can be used in the second alignment configuration to analyze for optical failures at the proximal and distal end of the light guides 322A as well as monitor the plasma generated by the plasma generator 333. The optical alignment system 357 can capture and analyze this data and determine whether to move the guide beam 324B to the next optical channel. If the optical alignment system 357 is nominal, then it aligns the guide beam 324B to the next channel and triggers the light source 324, repeating the process down the full array of the light guide bundle 322.

FIG. 4 is a simplified schematic view of a portion of an embodiment of the catheter system 400, including an embodiment of the optical alignment system 457, the optical alignment system 457 being utilized in a third alignment configuration.

The design of the catheter system 400 is substantially similar to the embodiments illustrated and described herein. It is appreciated that various components of the catheter system 400, such as are shown in FIG. 1, are not illustrated in FIG. 4 for purposes of clarity and ease of illustration. However, it is appreciated that the catheter system 400 can include most, if not all, of such components.

As shown in FIG. 4, the catheter system 400 again includes a light source 424 that is configured to generate light energy in the form of a source beam 424A, e.g., a pulsed source beam, that can be selectively and/or alternatively directed to and received by each light guide 422A (within the light guide bundle 422) as an individual guide beam 424B. Some or all of the optical elements can be configured to focus, reflect, and/or filter the source beam 424A as the individual guide beam 424B down onto a guide proximal end 422P of the light guide 422A, thereby coupling the individual guide beam 424B in the form of the pulse of infrared energy into the light guide 422A. The individual guide beam 424B, when aligned with the light guide 422A, travels toward the plasma generator 433.

In certain embodiments, as shown in FIG. 4, the source beam 424A from the light source 424 passes through, reflects off of, or otherwise interacts with, at least one optical element, such as one or more reflectors 460. Each reflector 460 can include one or more adjustable mirrors and/or mounted mirrors. In some embodiments, the reflector 460 can include one or more adjustment fasteners (not shown) that enable the positioning and/or adjustment of the reflector 460. It is appreciated that, in certain embodiments, one or more of the reflectors 460 can be fixed and immovable. In some embodiments, the optical alignment system 457 can further include one or more reflector movers 461.

Each reflector mover 461 can move one of the reflectors 460 to more accurately guide the source beam 424A and/or the individual guide beams 424B throughout the catheter system 400 and into the guide proximal end 422P of the light guide 422A. The reflector mover 461 can be controlled by the alignment controller 473 and/or the system controller 463.

Each reflector mover 461 can include one or more suitable actuators, such as a stepper motor, a piezoelectric actuator, or any other suitable type of actuator. The reflector mover 461 can move a corresponding reflector 460 with at least one, and up to six, degrees of freedom along and/or about the X, Y, and Z axes (not shown) of the reflector 460.

As illustrated in the embodiment of FIG. 4, the catheter system 400 can include the optics mover 470. The optics mover 470 can have the same and/or substantially similar functionality and/or components as described in the embodiments disclosed herein. For example, the optics mover 470 can include a stepper motor, a piezoelectric actuator, or any other suitable type of actuator.

Figure 5A:
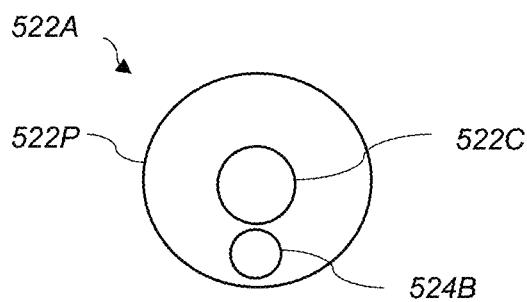
FIG. 5A is a simplified view of a guide proximal end of a light guide, and a portion of the guide beam reflected off the guide proximal end of the light guide, the portion of the guide beam being shown in an unaligned state.

FIG. 5A is a simplified view of a guide proximal end 522P, and a portion of the guide beam 524B reflected off the light guide 522A, the portion of the guide beam 524B being shown in an unaligned state. As shown in the embodiment illustrated in FIG. 5A, the unaligned state is when the portion of the guide beam 524 is not substantially within a guide center 522C of the light guide 522A. FIG. 5A shows the focused location of the guide beam 324B (illustrated in FIG. 3) that has been scattered off of the guide proximal end 322P (illustrated in FIG. 3). By adjusting the position of the light guide bundle and/or the guide beam 324, the scattered light can be captured by the camera 365 (illustrated in FIG. 3).

Figure 5B:
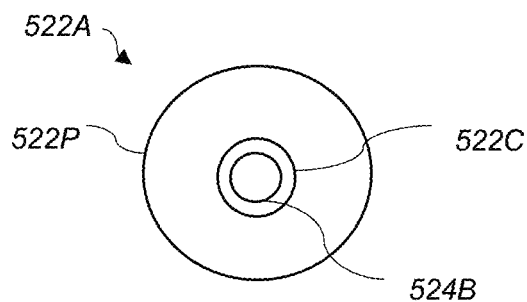
FIG. 5B is a simplified view of a guide proximal end of a light guide, and a portion of the guide beam reflected off the guide proximal end of the light guide, the portion of the guide beam being shown in an aligned state.

FIGS. 5A and 5B can illustrate a dual-imaging approach to optical alignment. FIGS. 5A and 5B can demonstrate some of the images captured by the camera 365 of the optical alignment system 357 (illustrated in FIG. 3).

FIG. 5B is a simplified view of a guide proximal end 522P, and a portion of the guide beam 524B reflected off the light guide 522A, the portion of the guide beam 524B being shown in an aligned state. In the embodiment shown in FIG. 5B, the portion of the guide beam 524B is shown in the aligned state, with the portion of the guide beam substantially within the guide center 522C of the light guide 522A. FIG. 5B demonstrates Fresnel reflection from fused silica surfaces within the light guide 522A, rather than the scattering depicted in FIG. 5A.

Figure 6:
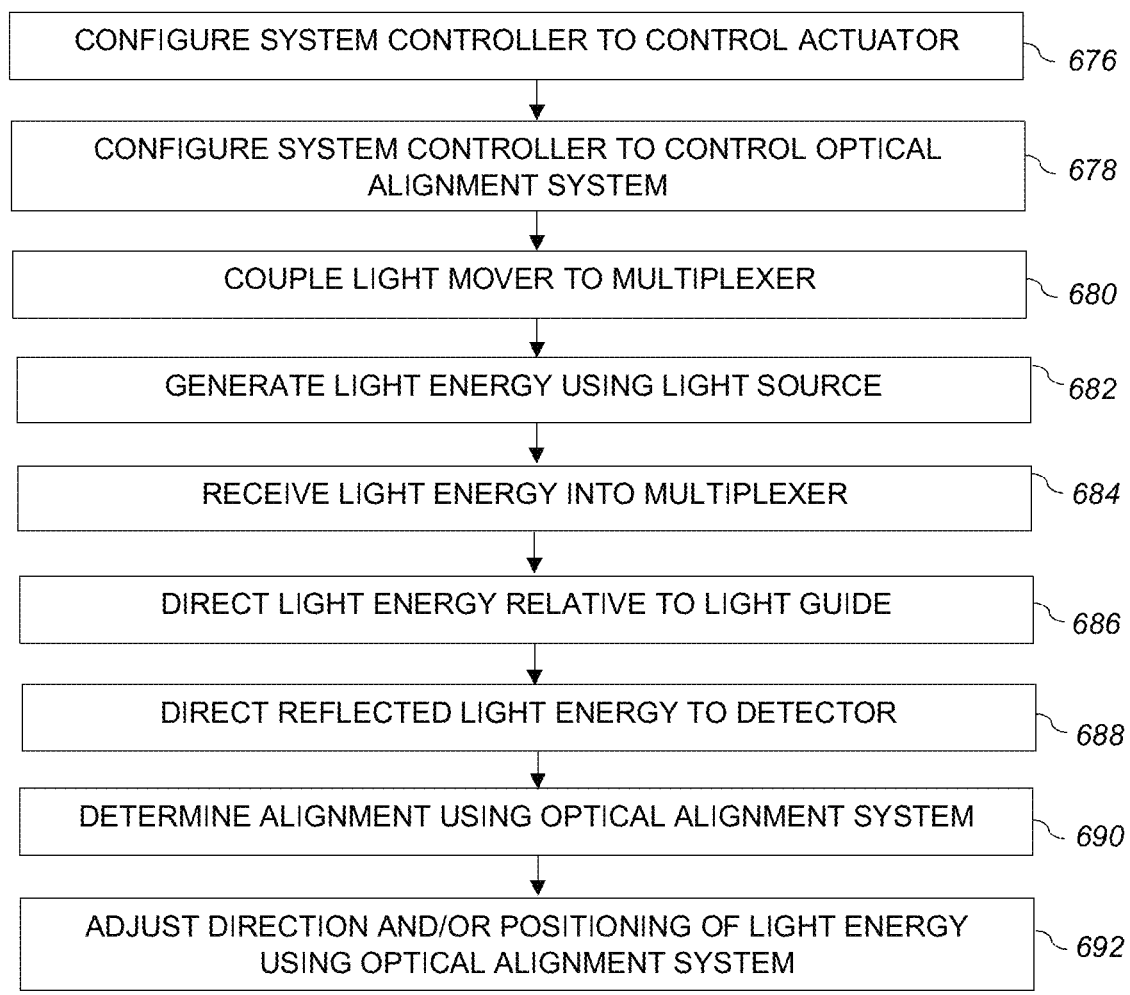
FIG. 6 is a flow chart of one embodiment of a method for treating a treatment site within or adjacent to a vessel wall or a heart valve using a catheter system having features and/or steps of the present invention.

FIG. 6 is a flow chart of one embodiment of a method for treating a treatment site within or adjacent to a vessel wall or a heart valve using a catheter system having features and/or steps of the present invention. It is understood that the method pursuant to the disclosure herein can include greater or fewer steps than those shown and described relative to FIG. 6. Stated another way, the method according to the present invention can omit one or more steps illustrated in FIG. 6 or add additional steps not shown and described in FIG. 6 and still fall within the purview of the present invention. Further, the sequence of the steps can be varied from those shown and described relative to FIG. 6. The sequence of steps illustrated in FIG. 6 is not intended to limit the sequencing of steps in any manner.

In the embodiment illustrated in FIG. 6, at step 676, a system controller is configured to control an optics mover.

At step 678, the system controller can be configured to control an optical alignment system and/or any component of the optical alignment system, such as a light source, a camera, an aligner, an amplifier, an illuminator, a detector, a filter, a beamsplitter, a camera controller, a signal processor, a multiplexer and/or a light guide bundle.

At step 680, a light mover is coupled to the multiplexer so the light mover can move the multiplexer. In some embodiments, the light mover is a linear translational stage.

At step 682, the light source generates light energy.

At step 684, the multiplexer receives the light energy generated by the light source.

At step 686, the multiplexer directs the light energy within a light guide.

At step 688, the light guide reflects a portion of the light energy back towards a detector.

At step 690, the detector or another component of the optical alignment system detects the alignment of the light energy and the light guide.

At step 692, the optical alignment system aligns the light energy with the light guide, so they are substantially coupled.

It is appreciated that the active detection and alignment of the coupling of the light energy with the light guide, through the use of the present invention, provides multiple advantages with respect to the performance, reliability, and proper usage of an IVL catheter, in particular one that utilizes an energy source to create a localized plasma which in turn produces a high energy bubble inside a balloon catheter. Specific advantages this invention provides include: 1) providing active compensation for connector and ferrule mechanical tolerances, thereby reducing system performance dependence on light carrier's mechanical tolerances and tolerances of their location in a multi-channel array, and 2) providing active compensation for drift in energy beam pointing that occurs in the source itself or through changes or motion of internal or coupling optics due to thermal drift or other factors. The active compensation ultimately reduces performance dependence on the accuracy of connecting and aligning the multi-channel array to the multiplexer and improves the speed and performance of the multiplexer and multi-channel ferrule system.

In particular, in various embodiments, the present invention comprises a multiplexer as a precision linear mechanism that translates coupling optics along a linear path. This approach can include a single degree of freedom. A ferrule can organize the individual optical fibers into a liner pattern with precise interval spacing. An example of a ferrule that can be used by the system is a V-groove ferrule block, as used in multi-channel fiber optics communication systems. The linear translation mechanism can be electronically controlled by the optical alignment system to line the beam path up sequentially with each individual fiber organized in the ferrule. The translating mechanism carries necessary beam directing optics and focusing optics to focus the laser energy onto each fiber to improve the optical coupling. By utilizing the systems and methods disclosed herein, the low divergence of the laser beam over the short distance of motion of the translated coupling mechanism has a minimum impact on coupling efficiency to the fiber. The optical alignment system can drive the mechanism to align the beam path with a selected fiber optic channel and then fires the laser in pulsed or semi-CW mode.

In other embodiments, the optical alignment system can incorporate secondary optics and an image sensor to directly image the ferrule block and the optical fibers. This subsystem simultaneously images the focused spot of the energy beam scattered off the ferrule or a strategically located nearby target. The image of the energy spot is in the same image reference frame allowing direct computation of offset from the core of the optical fiber. This data can be computed using image processing methods and algorithms to determine offset and compute compensation adjustment. A positioning mechanism can then adjust the positioning of the ferrule array to provide improved coupling of the focused spot to the fiber core.

The systems and methods disclosed in the various embodiments provided herein can be implemented on any multiplexer configuration, including linear, circular, patterned, or scanned configurations, provided that the wavelength separating beamsplitter can be inserted in the beam path between the coupling optics and the energy source. The systems and methods disclosed herein can enable the coupling lens to function in dual-use mode, both coupling energy into a light guide and part of the imaging lens to image the light guide.

It is appreciated that the systems and methods of optical alignment provided herein address multiple potential issues with the performance, reliability, and proper usage of an IVL catheter, in particular one that utilizes an energy source to create a localized plasma which in turn produces a high energy bubble inside a balloon catheter. Specific problems solved by the systems and methods disclosed herein include:

1) Complex laser systems with moving components suffer from beam pointing errors. These pointing errors can be induced by vibration, the thermal drift of optical components and mirrors, and long-term mechanical changes in mounting the source and optics. This drift in beam pointing can be angular or lateral and would create offsets in the focused spot location. Without compensation for these drifts, the error in spot location relative to the optical fiber core leads to a loss in coupling efficiency and damage to the fiber at high energies. The systems and methods disclosed herein provide active compensation for actual beam drift as it occurs at the point of coupling.
2) The systems and methods disclosed herein provide compensation for mechanical tolerance stack-ups of assemblies and true alignment for optical fibers, ferrule, connector, and receptacle, thereby making it possible to use low-cost, low-precision components on the SUD and improve COGS.
3) The systems and methods disclosed herein reduce the multiplexer performance dependence on the accuracy of static or fixed positioning mechanism in multiplexer and associated quality and precision of its optical and mechanical components, thereby improving the speed and performance of the multiplexer and multi-channel ferrule system.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the detailed description provided herein. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope, and no limitations are intended to the details of construction or design herein shown.

What is claimed is:

1. A catheter system for treating a treatment site within or adjacent to a vessel wall or a heart valve, the catheter system comprising:
a light source that generates light energy;
a first light guide that receives the light energy from the light source, the first light guide having a guide proximal end;
a second light guide that receives the light energy from the light source, the second light guide having a guide proximal end;
a multiplexer that directs the light energy toward the guide proximal end of the first light guide and the guide proximal end of the second light guide; and
an optical alignment system that determines an alignment of the light energy relative to at least one of the guide proximal ends, the optical alignment system adjusting a positioning of the light energy relative to the at least one of the guide proximal ends based at least partially on the alignment of the light energy relative to the at least one of the guide proximal ends, the optical alignment system including an imaging system including an imaging sensor that is configured to capture images of a focal point of the light source and the at least one of the guide proximal ends.

2. The catheter system of claim 1 wherein the imaging system is configured to simultaneously capture images of the focal point of the light source and a scattered energy beam scattered off the at least one of the guide proximal ends.

3. The catheter system of claim 1 wherein the imaging system is configured to utilize an image reference frame that allows direct computation of a distance offset from a center of the at least one of the guide proximal ends.

4. The catheter system of claim 3 wherein the imaging system is configured to determine the distance offset and compute a compensation adjustment of the alignment of the light energy relative to the at least one of the guide proximal ends.

5. The catheter system of claim 4 wherein the optical alignment system further includes an alignment positioner that positions the alignment of the light energy relative to the at least one of the guide proximal ends based on the computed compensation adjustment to substantially couple the light source and the at least one of the guide proximal ends.

6. The catheter system of claim 1 wherein the optical alignment system further includes a reflector and a reflector mover that moves the reflector.

7. The catheter system of claim 1 wherein the light source is a pulsed IR laser.

8. The catheter system of claim 1 wherein the optical alignment system further includes an illuminator that illuminates the at least one of the guide proximal ends to provide improved image quality and brightness.

9. The catheter system of claim 8, wherein the system controller controls the illuminator and adjusts an image brightness and contrast.

10. A catheter system for treating a treatment site within or adjacent to a vessel wall or a heart valve, the catheter system comprising:
a light source that generates light energy;
a first light guide that receives the light energy from the light source, the first light guide having a guide proximal end;
a second light guide that receives the light energy from the light source, the second light guide having a guide proximal end;
a multiplexer that directs the light energy toward the guide proximal end of the first light guide and the guide proximal end of the second light guide; and
an optical alignment system that determines an alignment of the light energy relative to at least one of the guide proximal ends, the optical alignment system adjusting a positioning of the light energy relative to the at least one of the guide proximal ends based at least partially on the alignment of the light energy relative to the at least one of the guide proximal ends, the optical alignment system including an imaging system including an imaging sensor that is configured to capture images of a focal point of the light source and the at least one of the guide proximal ends;
wherein the optical alignment system further includes one of a stepper motor and a piezo actuator that is configured to adjusts a yaw, pitch, and roll of at least one of the light guides.

11. The catheter system of claim 10 further comprising a system controller that is configured to control the optical alignment system so that the light energy is substantially coupled to the at least one of the guide proximal ends.

12. The catheter system of claim 10 wherein at least one of the light guides is an optical fiber and the light source is a laser.

13. The catheter system of claim 10 wherein the optical alignment system further includes an optical aligner that is configured to align the light energy with the at least one of the guide proximal ends.

14. The catheter system of claim 13 wherein the optical aligner is controlled by the system controller.

15. The catheter system of claim 10 further comprising a system controller that is configured to control an actuator that positions the multiplexer and aligns the light energy relative to the at least one of the guide proximal ends.

16. The catheter system of claim 10 wherein the light source is a pulsed IR laser.

17. The catheter system of claim 10 wherein the optical alignment system further includes optical compensators that are configured to adjust the positioning of the light source relative to the at least one of the guide proximal ends, the optical compensators including a plurality of optical steering wedges positioned in a path of the light source, the plurality of optical steering wedges being configured to improve a coupling of the light source and the at least one of the guide proximal ends.

18. The catheter system of claim 10 wherein the optical alignment system further includes a reflector and a reflector mover that moves the reflector.

19. The catheter system of claim 10 wherein the optical alignment system further includes an illuminator that illuminates the at least one of the guide proximal ends to provide improved image quality and brightness.

20. The catheter system of claim 19 wherein the system controller controls the illuminator and adjusts an image brightness and contrast.

* * * * *